United States Patent [19]
Winter et al.

[11] Patent Number: 5,552,379
[45] Date of Patent: Sep. 3, 1996

[54] AROMATIC COMPOUNDS, PROCESSES FOR THEIR PREPARATION AND THEIR USE IN PERFUMERY

[75] Inventors: Beat Winter, Sezenove/Bernex; Pierre-Alain Blanc, Crassier; Serge Lamboley, Bussigny, all of Switzerland

[73] Assignee: Firmenich SA, Switzerland

[21] Appl. No.: 439,754

[22] Filed: May 12, 1995

[30] Foreign Application Priority Data

May 31, 1994 [CH] Switzerland .................. 1689/94

[51] Int. Cl.⁶ .................. A61K 7/46; C07D 317/12; C07D 319/06; C07C 47/115
[52] U.S. Cl. .................. 512/12; 549/347; 549/369; 549/430; 568/440; 568/592; 514/18
[58] Field of Search .................. 568/440, 592; 512/12, 18; 549/347, 369, 430

[56] References Cited

FOREIGN PATENT DOCUMENTS

| A-1177132 | 6/1957 | France. |
| 2079751 | 7/1980 | United Kingdom. |
| WO94/27946 | 12/1994 | WIPO. |

OTHER PUBLICATIONS

Patent Abstracts of Japan, vol. 014, No. 555 (C-0786), Dec. 10, 1990.

*Primary Examiner*—Nicky Chan
*Attorney, Agent, or Firm*—Pennie & Edmonds

[57] ABSTRACT

The compounds of formula
a.

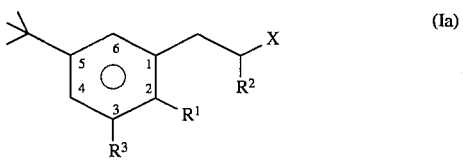

(Ia)

wherein symbol X represents a —CHO group or a group of formula

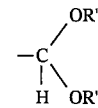

in which symbols R', taken separately, represent each a $C_1$ to $C_4$, linear or branched, saturated or unsaturated alkyl radical, or taken together represent a substituted or unsubstituted $C_2$ to $C_4$ alkylene radical; symbol $R^2$ represents a hydrogen atom or a methyl radical; and $R^1$ and $R^3$ are different and represent each a hydrogen atom or a methyl radical;
or of formula
b.

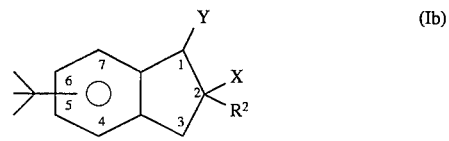

(Ib)

wherein the tert-butyl radical is located in position 5 or 6 of the aromatic ring and, either Y represents hydrogen and X and $R^2$ have the meaning indicated above, or X and $R^2$ represent each a hydrogen atom and Y represents a —CH₂CHO group or a group of formula

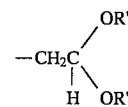

in which R' is defined as in a.;
or of formula
c.

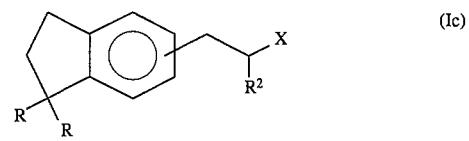

(Ic)

wherein X and $R^2$ have the meaning indicated in formula (Ia) and R represents a hydrogen atom or a methyl radical, the groups R being identical or different, are useful as perfuming ingredients for the preparation of perfuming compositions and perfumed articles to which they impart floral odor notes.

7 Claims, 2 Drawing Sheets

AROMATIC COMPOUNDS, PROCESSES FOR THEIR PREPARATION AND THEIR USE IN PERFUMERY

BRIEF DESCRIPTION OF THE INVENTION

The present invention relates to the field of perfumery. It concerns, in particular, novel aromatic compounds which are useful as perfuming ingredients, of formula
a.

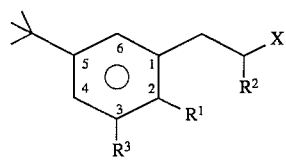
(Ia)

wherein symbol X represents a —CHO group or a group of formula

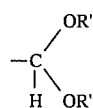

in which symbols R', taken separately, represent each a $C_1$ to $C_4$, linear or branched, saturated or unsaturated alkyl radical, or taken together represent a substituted or unsubstituted $C_2$ to $C_4$ alkylene radical; symbol $R^2$ represents a hydrogen atom or a methyl radical; and $R^1$ and $R^3$ are different and represent each a hydrogen atom or a methyl radical;
or of formula
b.

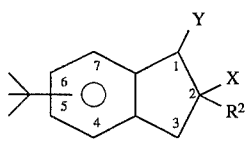
(Ib)

wherein the tert-butyl radical is located in position 5 or 6 of the aromatic ring and, either Y represents hydrogen and X and $R^2$ have the meaning indicated above, or X and $R^2$ represent each a hydrogen atom and Y represents a —$CH_2CHO$ group or a group of formula

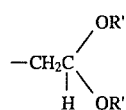

in which R' is defined as in a.;
or of formula
c.

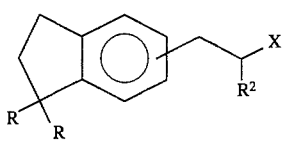
(Ic)

wherein X and $R^2$ have the meaning indicated in formula (Ia) and R represents a hydrogen atom or a methyl radical, the groups R being identical or different.

The invention also provides a method to confer, improve, enhance or modify the odor properties of a perfuming composition or a perfumed article, which method comprises adding to said composition or article a fragrance effective amount of a compound as mentioned above.

The invention further relates to the perfume compositions and perfumed articles which contain the above-mentioned compounds.

The invention also relates to a process for the preparation of a compound of formula

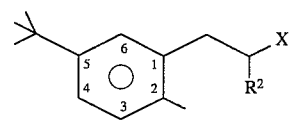
(I'a)

wherein symbols X and $R^2$ have the meaning indicated in formula (Ia), or of formula

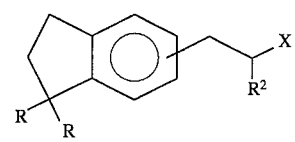
(Ic)

such as defined in claim 1, which process comprises:
a. hydrolyzing, by means of an add, an enol-ester of formula

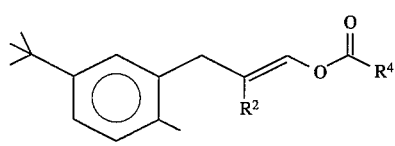
(IIa)

or respectively of formula

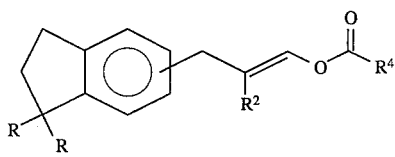
(IIc)

in which formulae R and $R^2$ have the meaning indicated above and symbol $R^4$ represents a $C_1$ to $C_3$ alkyl radical, to form the corresponding aldehyde (I'a), respectively (Ic); and b. where applicable, acetalyzing, in a generally known manner, said aldehyde thus formed to obtain the corresponding acetal.

The invention also provides a process for the preparation of a compound of formula

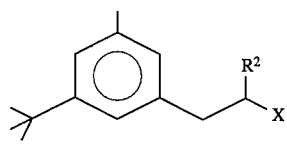
(I"a)

wherein X and $R^2$ are defined as in formula (Ia), which process comprises:
a. catalytically hydrogenating, in an inert organic solvent, an aldehyde of formula

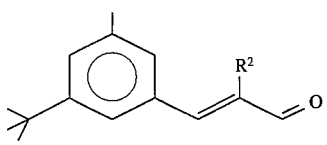

wherein R² has the meaning indicated above, to form the corresponding aldehyde (I"a); and b. where applicable, acetalyzing, in a generally known manner, said aldehyde (I"a) thus formed to obtain the corresponding acetal.

Yet another object of the invention is a process for the preparation of a compound of formula

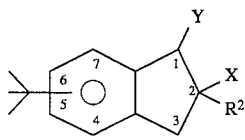

wherein the tert-butyl radical is located in position 5 or 6 of the aromatic ring and either Y represents hydrogen and X and R² are defined as in formula (Ia), or X and R² represent hydrogen and Y represents a —CH₂CHO or a group of formula

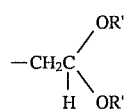

in which R' has the meaning indicated in formula (Ia), which process comprises:

a. treating with an oxidizing agent an alcohol of formula

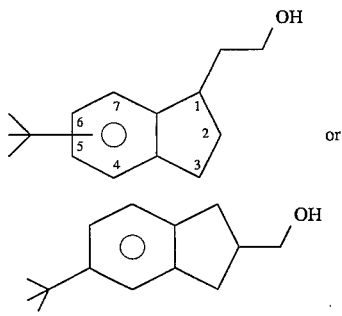

to form the corresponding aldehyde (Ib);

b. where applicable, methylating, in a generally known manner, the aldehyde obtained in a. which corresponds to alcohol (IVb) to form an aldehyde (Ib) of formula

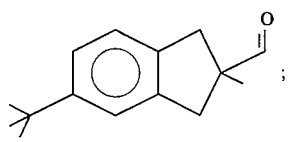

and c. where applicable, acetalyzing, in a generally known manner, said aldehyde (Ib) to form the corresponding acetal.

Finally, the compounds of formulae (II), (III) and (IV), used as starting products in these processes, are also the object of the invention.

BACKGROUND OF THE INVENTION

As is apparent from the following Table, there are a variety of prior known compounds whose structure is close to that of compounds (Ia), some of which have met with commercial success. Furthermore, several of these known compounds are described in the reference textbook of S. Arctander, Perfume and Flavor Chemicals, Montclair, N.J., USA (1969) and this is indicated in the table.

TABLE

| Compounds | Odor | Reference |
|---|---|---|
| | very strong, floral, lily of the valley | Naarden Int.- product sheet |
| | floral, green, lime-blossom | Arctander 496 |
| | floral, green, cucumber, melon, lime-blossom | Arctander 758 |
| | floral, sweet, green. fruity | Arctander 2741 |
| | floral, sweet, spicy | Arctander 2073 |
| | floral, green, lily of the valley | NL7905175 |
| | fresh, floral, fruity, melon, lily of the valley, lime-blossom | US 4'910'346 |

In spite of the abundance of known products of this type, the research activity in this field remains unflagging, namely with the aim of discovering compounds which have a wider variety of odor nuances and also compounds which have an enhanced stability in compositions, compared to that of the known compounds. It is in fact of general knowledge that these prior art aldehydes are very readily air-oxidized to form the corresponding acids, which are either odorless or possess disagreable odors, but, either way, no longer display the desired olfactive characters.

DETAILED DESCRIPTION OF THE INVENTION

Figure 1:
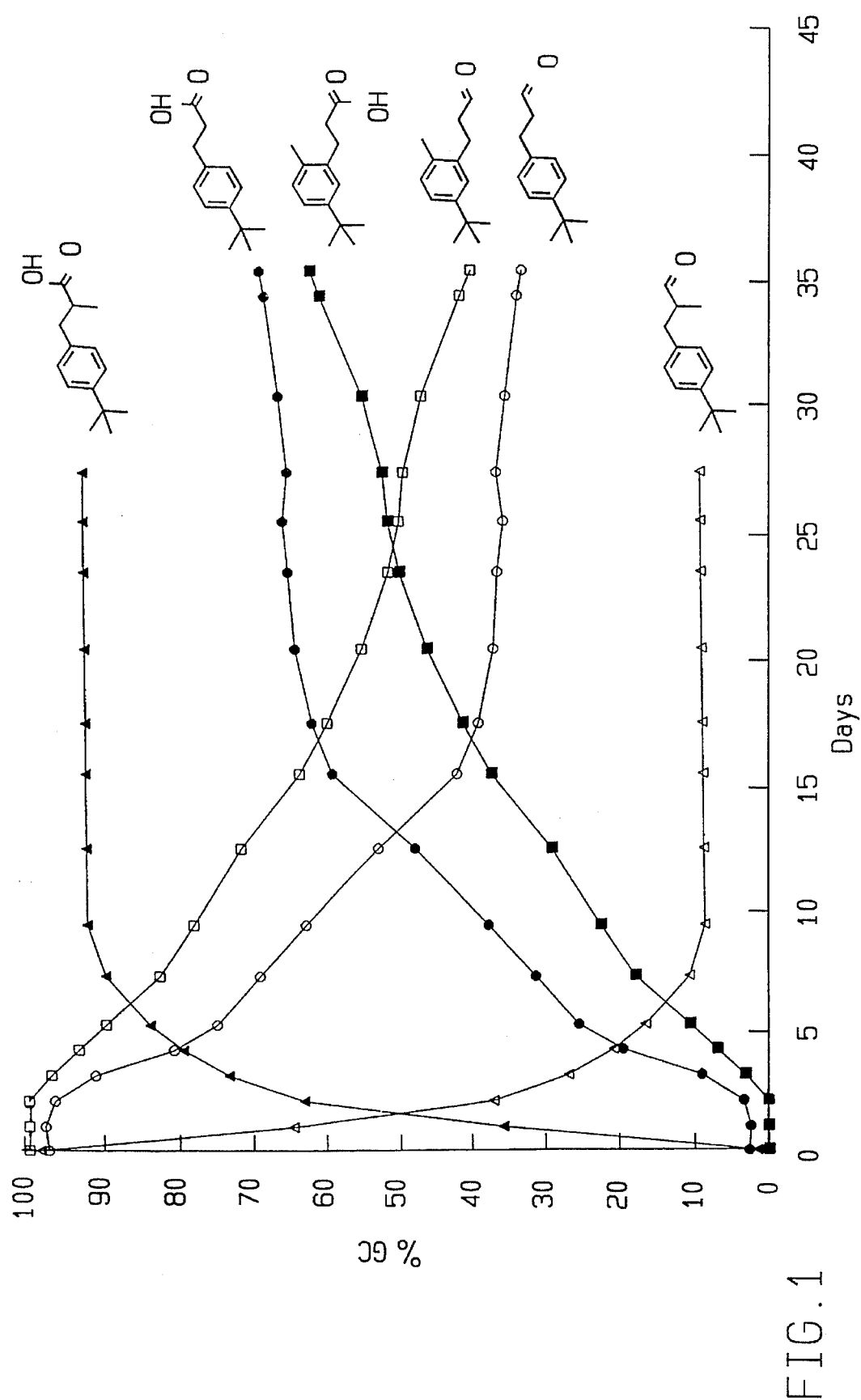

We have now surprisingly discovered that the above-mentioned compounds (Ia, b, c) possess very useful odor properties, which are also distinct from those of the prior art compounds, and that they are also advantageous from the point of view of stability against oxidation and fragrance tenacity. Namely, it has been established that certain preferred compounds of the invention are able to advantageously replace, in their typical applications, their known analogues, i.e.-(4-tert-butyl-1-phenyl)-2-methylpropanal, or LILIAL® (origin: Givaudan-Roure, Vernier, Switzerland), and 3-(4-tert-butyl-1-phenyl)propanal, or BOURGEONAL® (origin: Naarden Intl, Holland), and that they could be far more stable and tenacious than the latter when used for example in detergents and fabric softeners.

Thus, amongst the compounds of the invention, preferred products include 3-(5-tert-butyl-2-methyl-1-phenyl)propanal which develops a very powerful floral, green note, the character of which is reminiscent of the odor of thyme. Its chain-methylated homologue, i.e. 2-(5-tert-butyl-2-methylbenzyl)propanal, possesses a floral and very powerful lily of the valley type note, also of excellent tenacity.

Curiously, 3-(3-tert-butyl-5-methylphenyl)propanal and 3-(3-tert-butyl-5-methylphenyl)-2-methylpropanal, which are isomers of the above two compounds of the invention, develop entirely distinct odors, the first mentioned compound having a rooty, earthy odor, of the vetyver type, with a very powerful floral, green bottom note, and the second developing a prized ozone type odor.

Amongst the bicyclic compounds of formulae (Ib,c), preferred products include 5-tert-butyl-2-indancarbaldehyde, the odor of which is particularly strong and tenacious, floral, green, reminiscent of the odor of BOURGEONAL®, also possessing a watery-ozone nuance of great value. As for 5-tert-butyl-2-methyl-2-indancarbaldehyde, having a further methyl radical, it develops a very different fragrance, with a metallic, aldehydic, green character, also watery and vaguely phenolic.

Another compound preferred by the perfumers is 3-(3,3-dimethyl-5-indanyl)propanal, which has a green, ozone, floral, aldehydic odor, of rare strength and also very tenacious. Its odor note is instantly reminiscent of the fragrance of freshly washed, clean linen. As directly obtained from the synthesis described further on, this compound may be accompanied of a minor amount of its isomer 3-(1,1-dimethyl-5-indanyl)propanal, which develops a similar odor, such that the mixtures of these two compounds have an olfactive character of the type here-above described.

Yet another preferred compound of the invention is 6-tert-butyl-1-indanacetaldehyde, the odor of which resembles that of 5-tert-butyl-2-indancarbaldehyde cited above, while possessing a more pronounced cresylic note and a greener, more anisic nuance, also less aldehydic-lily of the valley than the latter.

One can still cite, as a preferred compound, 3-(5-indanyl)propanal, which develops an aldehydic odor of the BOURGEONAL® type, remarkably powerful and with a citrus bottom note. This compound can also be used to the same effect in admixture with its isomer 3-(4-indanyl)propanol.

It is apparent from the preceding considerations that the compounds of the invention bring a new and varied range of odor nuances to the perfumers' palette, while retaining certain of the odor characters most appreciated in the prior art compounds of similar structure cited in the Table above.

On the other hand, as shown in the examples presented further on, it has been discovered that the compounds (Ia), whose structure is closer to that of the prior art products, turn out to be far more stable against oxidation than the latter and possess far more tenacious fragrances, which renders their use in particularly agressive media such as detergents and household products distinctly advantageous.

This result of our studies was all the more unexpected in that, in spite of the large number of new compounds prepared during these studies, some fifty or more, by varying the nature and the position of the substituent groups and the nature of the functional group (ester, ether and nitrile derivatives having also been prepared), few really attracted the perfumers' interest, and amongst which compounds (Ia, b, c) showed exceptional odor properties and, particularly those wherein $R^2$ represents a hydrogen atom, better stability than the known compounds. These advantageous properties appeared as a result of ingenious olfactive evaluations carried out by panels of expert perfumers, who discovered with surprise the superiority of the odor properties of the compounds of the invention, which superiority was quite clear not only on smelling strip evaluations of each pure product or of compositions containing it, but also when said product was applied for perfuming detergents and fabric softeners in particular.

The compounds of the invention can be used with equal advantage in both fine and technical perfumery and, as a result of their odor qualities, their use is far more general than that of the known compounds, namely known p-tert-butyl-α-methyl-hydrocinnamic aldehyde. They are useful to prepare perfuming bases and perfumes and to perfume a variety of consumer products such as soaps, bath and shower gels, shampoos and other hair-care products, cosmetic preparations and body or air deodorants. In addition, as a result of the strength and tenacity of their odor note, 5-tert-butyl-2-indancarbaldehyde and 3-(3,3-dimethyl-5-indanyl)propanal in particular revealed themselves to be of an extremely advantageous use for perfuming detergents and fabric softeners. Household products can also be perfumed by means of compounds (Ia, b, c).

In these applications, the compounds of the invention can be used in a wide range of concentrations. One can cite, by way of example, concentrations of the order of 5 to 10%, even 15 or 20% by weight, relative to the weight of the composition into which they are incorporated.

It is clear however that such values are only indicative, since the concentrations of compound (I) are dependent on the olfactive effect that is desired to achieve, as well as on the nature of the product to be perfumed. In addition, they are also a function of the nature of the other ingredients present in a given composition whenever compounds (I) are used in admixture with solvents, adjuvants and perfuming co-ingredients of current use in perfumery, examples of which can be found in reference textbooks such as the work of S. Arctander, Perfume & Flavor Chemicals, Montclair, N.J., USA (1969).

Concentration values well below those dated above, of the order of 0.1 to 0.5% by weight, relative to the weight of the composition into which they are incorporated, will generally be used when compounds (I) are employed for perfuming the various consumer products mentioned above.

The invention also relates to a process for the preparation of a compound of formula

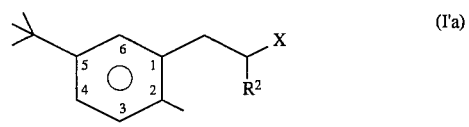

(I'a)

wherein symbols X and $R^2$ have the meaning indicated in formula (Ia), or of formula

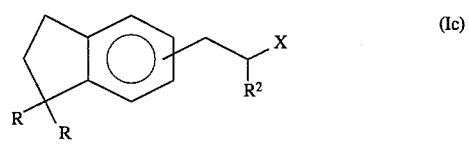

(Ic)

as previously defined, which process comprises:

a. hydrolyzing, by means of an acid, an enol-ester of formula

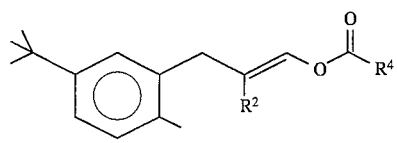

(IIa)

or respectively of formula

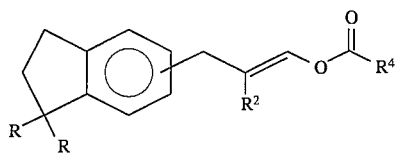

(IIc)

in which formulae R and $R^2$ have the meaning indicated above and symbol $R^4$ represents a $C_1$ to $C_3$ alkyl radical, to form the corresponding aldehyde (I'a), respectively (Ic); and b. where applicable, acetalyzing, in a generally known manner, said aldehyde thus formed to obtain the corresponding acetal.

The hydrolysis of esters (IIa) and (IIc) is carried out under conventional conditions, by means of any acid of current use in this type of reactions [see for example, J. March, Advanced Organic Chemistry, 3rd ed., section 0–11, John Wiley & Sons, USA (1985)]. The detailed conditions of these reactions are described in the preparation examples presented further on. Compounds of formula (IIa) or (IIc) wherein $R^4$ represents a methyl radical are preferably used.

The latter are novel compounds which are also the object of the invention. Compounds (IIa) can be prepared from benzene derivatives of commercial origin and compounds (IIc) starting from the appropriate indane [see M. T. Bogert and al., J. Amer. Chem. Soc. 56, 185 (1934); S. T. Bright and al., J. Org. Chem. 55, 1338 (1990)] via condensation with an unsaturated diacetate [see, for example, I. Scriabine, Bull. Soc. Chim. France 1961, 1194; N. E. Kologrivova and al., C.A. 78, 88513p (1973)].

SCHEME I

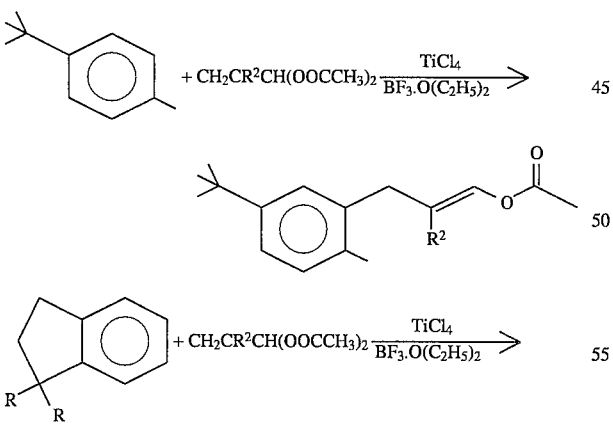

-continued
SCHEME I

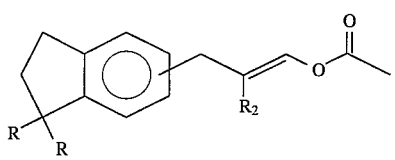

R, $R^2$ = H, $CH_3$

The conditions of these condensation reactions are described in detail in the examples presented further on.

The invention also relates to a process for the preparation of a compound of formula

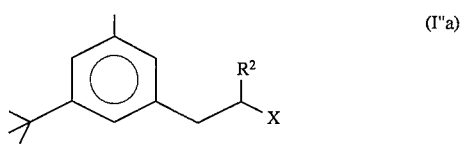

(I"a)

wherein X and $R^2$ are defined as in formula (Ia), which process comprises:

a. catalytically hydrogenating, in an inert organic solvent, an aldehyde of formula

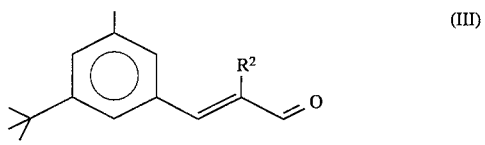

(III)

wherein $R^2$ has the meaning indicated above, to form the corresponding aldehyde (I"a); and b. where applicable, acetalyzing, in a generally known manner, said aldehyde (I"a) thus formed to obtain the corresponding acetal.

The hydrogenation reaction takes place in the presence of a catalyst such as Pd-C, under classical conditions, described further on in a detailed manner.

The starting products of formula (III) are novel compounds, prepared from 5-tert-butyl-1,3-dimethylbenzene, according to the following scheme:

SCHEME II

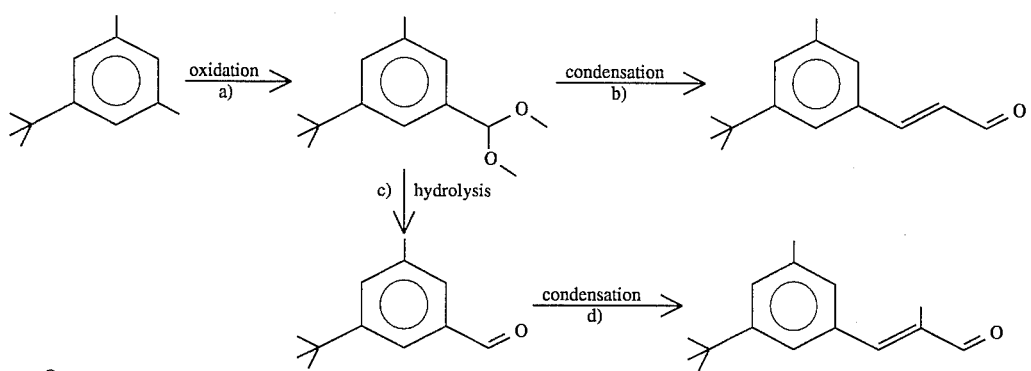

a) -e⊖/C/Inox, sodium p-toluenesulfonate, CH$_3$OH
b) i) CH$_3$CH$_2$OCHCH$_2$, ZnCl$_2$, H$_3$PO$_4$, 0–5° C.
   ii) HCOOH, HCOONa, H$_2$O, 90–110° C.
c) 10% aq. HCl, THF, r.t.
d) CH$_3$CH$_2$CHO, K$_2$CO$_3$, CH$_3$OH, 65° C.

We observed that the reaction of condensation of the intermediate acetal [step b), see for example, H. von der Bruggen and al., J. Org. Chem. 1983, 2920 and refs. there-cited] was best carried out in the presence of zinc chloride and phosphoric add.

The reactions represented in this scheme are described in further detail in the examples presented further on.

If desired, the aldehydes of formula (I'a) and (I"a), obtained as described above, can be converted into the corresponding acetals by way of methods well-known to the skilled person, for example by reacting said aldehydes with appropriate alcohols or diols, in the presence of an acidic catalyst [see for example, J. March, Advanced Organic Chemistry, section 6–6, 3rd ed., John Wiley & Sons, USA (1985)]. The detailed conditions of these acetalyzation reactions are described in the preparation examples appearing further on.

The bicyclic compounds of formula (Ib) according to the invention are prepared following an original process which comprises:

a. treating with an oxidizing agent an alcohol of formula

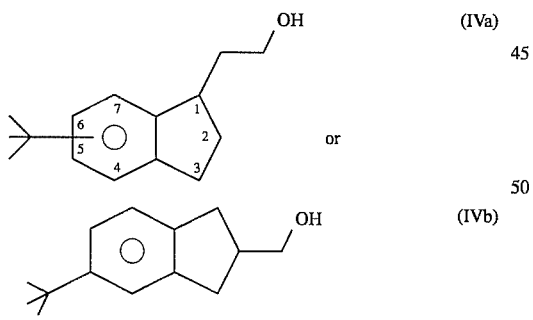

to form the corresponding aldehyde (Ib);

b. where applicable, methylating, in a generally known manner, the aldehyde obtained in a. which corresponds to alcohol (IVb) to form an aldehyde (Ib) of formula

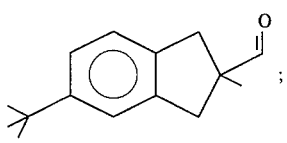

and c. where applicable, acetalizing, in a generally known manner, said aldehyde (Ib) to form the corresponding acetal.

The reactions of oxidation of compounds (IV) take place under conventional conditions, for example by means of pyridinium chlorochromate (PCC) as oxidizing agent.

The formula (IV) alcohols are novel compounds which can be prepared in a classical manner, as represented hereafter for the compounds (IV) having the tert-butyl radical in position 5 of the aromatic ring.

SCHEME III

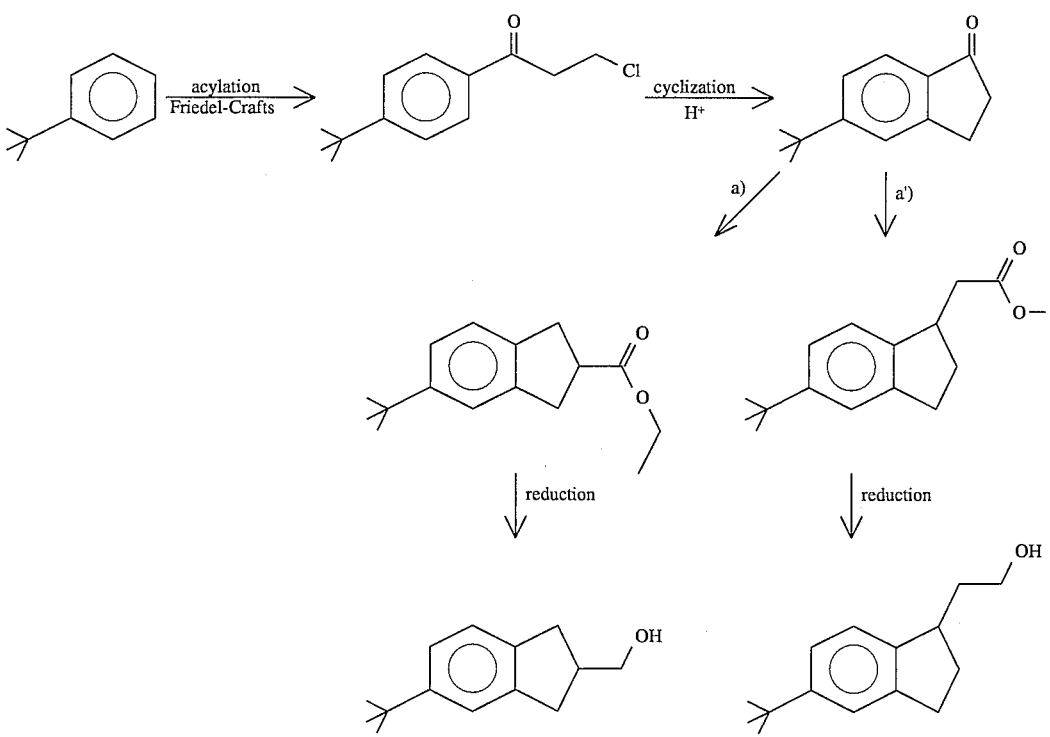

a) i) NaH, (CH₃CH₂O)₂CO, toluene, 60° C.
   ii) H₂, 5% Pd—C, ethyl acetate, r.t.
a') i) (CH₃O)₂POCH₂COOCH₃, NaOCH₃, petroleum ether 30–50, r.t.
   ii) H₂, 5% Pd—C, ethyl acetate, r.t.

These reactions are described in further detail in the preparation examples presented further on.

The aldehydes (Ib) according to the invention can then be converted into the corresponding acetals as described above.

The invention will now be described in greater detail by way of the following examples, wherein the temperatures are indicated in degrees Celsius and the abbreviations have the usual meaning in the art.

EXAMPLE 1

Preparation of 3-(5-tert-butyl-2-methyl-1-phenyl)propanal

To a solution of 3-(5-tert-butyl-2-methyl-1-phenyl)-1-propenyl acetate (mixture Z/E ~1:10; 0.68 g, 2.7 mmole) in tetrahydrofuran (THF, 8 ml), kept under stirring, there was added aq. 25% $H_2SO_4$ (2 ml) and the mixture was heated to reflux (65°) during 2 h. It was then diluted with ether and brine, the organic phase was washed with sat. $NaHCO_3$ and brine, dried over $Na_2SO_4$ and concentrated (0.62 g). After bulb-to-bulb distillation (oven temp. 160°/0.5×10² Pa), there was obtained 3-(5-tert-butyl-2-methyl-1-phenyl)propanal as a colorless oil (0.54 g, purity 96%, yield 96%).

IR(neat): 2950, 2890, 2850, 2700, 1720, 1495, 1450, 1355, 1265, 1130, 820 cm⁻¹

NMR($^1$H, 360 MHz, CDCl₃): 9.85(t, J=1, 1H); 7.16(dd, $J_1$=8, $J_2$=2, 1H); 7.14 (broad s, 1H); 7.09(d, J=8, 1H);2.94(t, J=8, 2H); 2.74(t, J=8, 2H); 2.28(s, 3H); 1.30(s, 9H)δ ppm NMR($^{13}$C, 90.5 MHz, CDCl₃): 201.6(d); 149.8(s); 138.0(s); 132.8(s); 130.2(d); 125.7(d); 123.4(d); 44.3(t); 34.3(s); 31.4(3q); 25.9(t); 18.7(q)δ ppm MS: 204(M⁺, 16), 189(94), 171(9), 145(100), 128(16), 115(27), 105(18), 91(25) 77(13), 57(11), 41(13)

Odor: described above.

The starting 3-(5-tert-butyl-2-methyl-1-phenyl)-1-propenyl acetate was prepared as follows.

To a stirred solution of 4-tert-butyl-toluene (Fluka, purity 95%, 18.1 ml, 10 mmole) in $CH_2Cl_2$ (10 ml), at room temperature, there was added $TiCl_4$ (Fluka puriss., 1.21 ml, 11 mmole) and $BF_3 \cdot O(C_2H_5)_2$ (30 ml, 1 mmole). The orange solution was cooled to −78° and a solution of acrolein diacetylacetal (Fluka purum 98%, 1.66 ml, 11 mmole) in $CH_2Cl_2$ (5 ml) was added dropwise. The reaction mixture was allowed to return to 0° and stirred during 15 min at this temperature. It was poured on a mixture of ice, aq. 10% HCl and ether, and the organic phase was washed with brine (2 times), sat. $NaHCO_3$ and brine. It was dried over $Na_2SO_4$, concentrated (2.52 g) and bulb-to-bulb distilled (90°/2 Pa) to provide the desired acetate as a yellow oil (1.64 g, purity 95%, Z/E ~1:10, yield 63%).

IR(neat): 3070, 3015, 2960, 2900, 2860, 1750, 1665, 1365, 1270, 1220, 1185, 1100, 945, 900, 820 cm⁻¹

NMR($^1$H, 360 MHz, CDCl3): isomer E 7.20–7.05(m, 4H); 5.57(dt, $J_1$=12, $J_2$=7, 1H); 3.31 (d, J=7, 2H); 2.27(s, 3H), 2.11(s, 3H); 1.30(s, 9H)δ ppm NMR($^{13}$C, 90.5 MHz, CDCl₃):isomer Z 168.1(s); 149.1(s); 137.2(s); 136.4(s); 133.0(s); 130.0(d); 125.8(d); 123.4(d); 113.4(d); 34.4(s); 31.6(t); 31.4(3q); 20.6(q); 18.7(q)δ ppm MS: 246(M⁺, 14), 231(7), 204(8), 189(68), 171(12), 147(27), 129(10), 115(11) 105(8), 91(11), 77(5), 57(28), 43(100)

Odor: green, vegetable, floral.

EXAMPLE 2

Preparation of 2-(5-tert-butyl-2-methylbenzyl)propanal

To a stirred solution of 3-(5-tert-butyl-2-methyl-1-phenyl)-2-methyl-1-propenyl acetate (26 g, 94 mmole, purity 94%) in methanol (60 ml) was added $K_2CO_3$ (1.38 g, 10 mmole). There was a slow exothermy and the temp. of the mixture was maintained below 35° with a water bath. After 1 h at 25°, GC analysis indicated complete disappearance of the starting acetate. The mixture was then diluted with ether, washed with sat. $NaHCO_3$ and brine, dried over $Na_2SO_4$ and concentrated to a yellow oil (20.8 g). Distillation on a 15 cm Vigreux column under reduced pressure gave the desired 2-(5-tert-butyl-2-methylbenzyl)propanal (18.8 g, purity 89%, yield 92%).

IR(neat): 2970, 2910, 2890, 2810, 2710, 1725, 1500, 1460, 1365, 1275, 1145, 825 cm$^{-1}$ NMR($^1$H, 360 MHz, CDCl$_3$): 9.73(d, J=2, 1H); 7.16(dd, J$_1$32 8, J$_2$=2,1H); 712(d, J=2, 1H); 7.08(d, J=8, 1H); 3.10(dd, J$_1$=14, J$_2$=6, 1H); 2.65(m, 1 H); 2.56(dd, J$_1$=14, J$_2$=8, 1H); 2.28(s, 3H); 1.30(s, 9H); 1.12(d, J=7, 3H)δ ppm NMR($^{13}$C, 90.5 MHz, CDCl$_3$): 204.5(d); 148.9(s); 136.6(s); 133.0(s); 130.2(d); 126.8(d); 123.4(d); 47.0(d); 34.3(s,t); 31.4(3q); 18.9(q); 13.5(q)δ ppm MS :218(M$^+$, 15), 203(72), 185(13), 161(41), 145(100), 131 (22), 115(22), 105(26), 91(25), 77(13), 57(28), 41(27)

Odor: described above.

The starting 3-(5-tert-butyl-2-methyl-1-phenyl)-2-methyl-1-propenyl acetate was prepared as follows.

To 4-tert-butyl-toluene (88.8 g, 0.6 mole) at 0° there was added TiCl4 (Fluka puriss., 38.0 g, 21.9ml, 200 mmole) and BF$_3$. O(C$_2$H$_5$)$_2$ (0.5 ml, 0.56 g, 4 mmole). The stirred mixture was cooled to −15° (dry ice-acetone bath) and a solution of methacrolein diacetylacetal (Fluka purum, 34.4 g, 200 mmole) in 4-tert-butyl-toluene (30 ml) was added dropwise during 0.5 h, while maintaining the temperature between −10° and −20°. The reaction mixture was then stirred during 30 min between −10° and +10° and diluted with ether. It was washed with aq. 10% HCl, brine (2 times), sat. aq. NaHCO$_3$ and brine. It was dried over Na$_2$SO$_4$, and concentrated under reduced pressure (142 g). Vacuum distillation on a 15 cm Vigreux column gave a first fraction containing 98% of 4-tert-butyl-toluene (98.6 g). The second fraction (bath temp. 180°–210°/0.6×10$^2$ Pa) contained the desired acetate (29.6 g, purity 86%, Z/E ~2:84, yield 49%).

IR(neat): 2955, 2900, 2860, 1745, 1675, 1360, 1225, 1100, 1090 cm$^{-1}$

NMR($^1$H, 360 MHz, CDCl$_3$): 7.16(dd, J$_1$=8, J$_2$=2, 1H); 7.13(d, J=2, 1H); 6.88(s, 1H); 3.27(s, 2H); 2.26(s, 3H); 2.13(s, 3H); 1.64(s, 3H); 1.30(s, 9 H)δ ppm NMR($^{13}$C, 90 MHz, CDCl$_3$): 168.3(s); 148.71(s); 136.1(s); 133.6(s); 130.0(d); 126.6(d); 123.3(d); 120.7(s); 38.0(t); 34.3(s); 31.4(3q); 20.8(q); 18.9(q); 13.9(q)δ ppm MS: 260(M+,15), 218(25), 203(72), 185(13), 161(41), 145(15), 133(30), 115(14), 105(13), 77(6), 57(32), 43(100), 29(11)

EXAMPLE 3

Preparation of 4-tert-butyl-2-(3,3-dimethoxypropyl)-1-methylbenzene

To a solution of 3-(5-tert-butyl-2-methyl-1-phenyl)propanal (1.06 g, 5 mmole) in methanol (10 ml), at room temperature, there was added conc. HCl (3 drops). After 3 h, the solution was poured into a mixture of ether and sat. NaHCO$_3$ for extraction. The organic phase was washed with NaHCO3, dried over K$_2$CO$_3$ and concentrated (1.25 g). After bulb-to-bulb distillation (120°/6 Pa), the desired product was obtained with 95% purity (1.2 g, yield 91%) and presenting the following analytical characters:

IR(neat): 2980, 2920, 2890, 2840, 1510, 1465, 1390, 1370, 1280, 1200, 1140, 1090, 1065, 920, 830 cm$^{-1}$ NMR($^1$H, 360 MHz, CDCl$_3$): 7.17(d, J=2, 1H); 7.14(dd, J$_1$=8, J$_2$=2, 1H); 7.08(d, J=8, 1H); 4.42(t, J=6, 1H); 3.35(s, 6H); 2.66(m, 2H); 2.28(s, 3H); 1.89(m, 2H); 1.30(s, 9H)δ ppm NMR($^{13}$C, 90.5 MHz, CDCl$_3$): 148.9(s); 139.3(s); 132.9(s); 130.0(d); 125.9(d); 122.9(d); 104.2(d); 52.8(2q); 34.3(s); 33.1(t); 31.5(q); 28.6(t); 18.7(q) δ ppm MS: 250(M$^+$,<1), 235(1), 218(14), 203(20), 186(22), 171 (56), 161(43), 145(24) 131(43), 106(18), 91(15), 75(100), 57(22), 41(15)

Odor: floral, pleasant.

EXAMPLE 4

Preparation of 5-tert-butyl-2-indancarbaldehyde

To a suspension of pyridinium chlorochromate (PCC, Fluka, 3.24 g, 15 mmole) in dichloromethane (20ml), there was added at room temperature, a solution of 5-tert-butyl-2-indanmethanol (2.04 g, 10 mmole) in dichloromethane (10 ml). The mixture was stirred for 5 h at room temperature. It was diluted in ether (50 ml), filtered on CELITE®, then on a FLORISIL® column (Fluka), and concentrated. Bulb-to-bulb distillation provided 5-tert-butyl-2-indancarbaldehyde (1.47 g, purity>99%, yield 72%) as a colorless oil.

NMR($^1$H, 360 MHz, CDCl$_3$): 9.77(d, J=2, 1H); 7.27(s, 1H); 7.22(d, J=8, 1H); 7.16(d, J=8, 1H); 3.35–3.10(m, 5H); 1.31(s, 9H)δ ppm NMR($^{13}$C, 90.5 MHz, CDCl$_3$): 203.0(d); 150.1(s); 141.0(s); 138.1(s); 124.1(d); 124.0(d); 121.5(d); 50.9(d); 34.6(s); 33.1 (t); 32.5(t); 31.5(q)δ ppm MS: 202(M$^+$, 36), 187(100), 169(10), 157(10), 141(11), 129 (18), 115(19), 91(6), 77(3), 57(6), 41 (6)

Odor: described above.

The starting alcohol was prepared according to Scheme III, as follows.

a) 5-tert-butyl-1-indanone

To a solution of tert-butylbenzene (88.9 g, 0.7mole) and of 3-chloropropionyl chloride (Fluka, 93.8 g, 0.7 mole) in CH$_2$Cl$_2$ (105 ml), at 0°, there was added portionwise AlCl$_3$ (95.7 g, 0.7 mole) over 2 h. After 3 h at 0°, the mixture was poured on ice and diluted with CH$_2$Cl$_2$ (200 ml). The organic phase was washed with water (2 times) and concentrated. The residue was dissolved in ether, washed with aq. sat. NaHCO$_3$ and brine, dried over Na$_2$SO$_4$ and concentrated (152 g). Crystallizing in petroleum ether 30°–50°, at −30°, provided colorless crystals (117 g, purity>99%, yield 52%) of 1-(4-tert-butyl-1-phenyl)-3-chloro-1-propanone. M.p. 35–37°

NMR($^1$H, 360 MHz, CDCl$_3$): 7.90(d, J=8, 2H); 7.49(d, J=8, 2H); 3.92(t, J=7, 2H; 3.43(t, J=7, 2H); 1.34(s, 9H)δ ppm NMR($^{13}$C, 90.5 MHz, CDCl$_3$): 196.2(s); 157.3(s); 133.7(s); 128.0(2d); 125.7(2d); 41.1(t); 38.8(t); 35.1(s); 31.0(3q)δ ppm MS: 224(M$^+$, 4), 209(13), 173(9), 161(100), 146(7), 118(9), 91(11), 77(4), 63(5), 41(2)

This propanone (116 g, 0.51 mole) was dissolved in conc. H$_2$SO$_4$ (920 ml) and heated to 100° under stirring (release of HCl). After 1.5 h, the mixture was cooled and poured on a mixture of ice (3.0 kg), NaCl (230 g) and ether (400 ml), the organic phase was washed with H$_2$O, aq. sat. NaHCO$_3$ and brine, dried over Na$_2$SO$_4$ and evaporated (97 g). Crystallizing from petroleum ether 30°–50°, at −30°, provided colorless crystals (74 g, purity>99%) of 5-tert-butyl-1-indanone. M.p 39–40°

IR(CHCl$_3$): 2960, 2880, 1708, 1603, 1325, 1085, 710 cm$^{-1}$

NMR(¹H, 360 MHz, CDCl₃): 7.69(d, J=8, 1H); 7.48(s, 1H); 7.43(d, J=8, 1H); 3.12(t, J=6, 2H); 2.67(m, 2H); 1.36(s, 9H)δ pm

NMR(¹³C, 90.5 MHz, CDCl₃): 206.5(s); 158.8(s); 155.5(s); 134.8(s); 125.0(d); 123.3(d); 123.2(d); 36.5(t); 35.4(s); 31.2(q); 25.9(t)δ ppm MS: 188(M⁺, 31), 173(100), 145(23), 131(29), 115(12), 103 (3), 91(8), 77(5), 51(3), 41(3)

Odor: vaguely cresolic.

b) ethyl 5-tert-butyl-2-indancarboxylate

A dispersion of NaH (80% in oil, 4.32 g, 144 mmole NaH) was washed with pentane, and toluene (140 ml) and diethyl carbonate (34 g, 288 mmole) were added thereto. The mixture was heated to 60° and there was added over 2 h a solution in toluene (20 ml) of the indanone prepared in a) (7.52 g, 40 ml). The reaction mixture was kept under stirring at 60° for 6 h.

It was poured on an excess of H₂O/CH₃COOH 1:1 and extracted with petroleum ether 30–50°, washed with aq. sat. NaHCO₃ and brine, dried over Na₂SO₄ and concentrated (10.8 g). After bulb-to-bulb distillation (150°/10 Pa), there were obtained 7.12 g of ethyl 5-tert-butyl-1-oxo-2indancarboxylate.

IR(neat): 2960, 2860, 1730–1700, 1598, 1360, 1320, 1250, 1205, 1150, 1080, 1010 cm⁻¹

NMR(¹H, 360 MHz, CDCl₃): 77.0(d, J=8, 1H); 7.50(s, 1H); 7.45(d, J=8, 1H); 4.25(q, J=7, 2H); 3.71(dd, J₁=8, J₂=4, 1H); 3.54(dd, J₁=17, J₂=4, 1H); 3.35(dd, J₁=17, J₂=8, 1H); 1.36(s, 9H); 1.32(t, J=7, 3H)δ ppm NMR(¹³C, 90.5 MHz, CDCl₃): 199.2(s); 169.4(s); 159.8(s); 154.0(s); 132.9(s); 125.6(d); 124.3(d); 123.0(d); 61.6(t); 53.6(d); 35.5(s); 31.1(3q); 30.4(t); 14.2(q)δ ppm MS: 260(M⁺, 61), 245(25), 215(24), 199(60), 186(77), 171 (100), 157(16) 143(11), 131(34), 115(31), 91(18), 57(76), 41(31)

A solution of this compound (4.68 g, 16.2 mmole) in ethyl acetate (50 ml) was stirred at room temperature, in the presence of 5% Pd/C (0.48 g) under H₂ (1 atm) during 12 h. The catalyst was filtered on CELITE® and the solution concentrated (4.25 g). Chromatography on SiO₂ (106 g) with pentane/ether 9:1 as eluting agent and bulb-to-bulb distillation (160°/5 Pa) provided the desired ethyl 5-tert-butyl-2-indancarboxylate (3.47 g, purity >99%, yield 86%).

NMR(¹H, 360 MHz, CDCl₃): 7.24(s, 1H); 7.20(d, J=8, 1H); 7.13(d, J=8, 1H); 4.18(q, J=7, 2H); 3.40–3.10(m, 5H); 1.31(s, 9H); 1.28(t, J=7, 3H)δ ppm NMR(¹³C, 90.5 MHz, CDCl₃): 175.4(s); 149.8(s); 141.5(s); 138.7(s); 123.8(d); 123.7(d); 121.2(d); 60.6(t); 43.8(t); 36.3(t); 35.8(t); 34.5(s); 31.6(3q); 14.3(q)δ ppm MS: 246(M⁺, 25), 231(100), 201(3), 172(25), 157(60), 129 (20), 115(20), 91(4) 79(4), 57(20), 41(7)

Odor: floral, lily of the valley, hydroxycitronellal.

c) 5-tert-butyl-2-indanmethanol

To a suspension of LiAlH₄ (0.27 g, 7.2 mmole) in ether (10 ml), at room temperature, there was added a solution of the carboxylate obtained according to b) (2.2 g, 8.9 mole) in ether (10 ml). Reaction was allowed under stirring for 2 h, at room temperature. The mixture was diluted in ether, poured on H₂O and the organic phase was washed with 10% aq. HCl, H₂O, sat. NaHCO₂ and brine. It was dried over Na₂SO₄, concentrated and bulb-to-bulb distilled (200°/40 Pa) to give the above-mentioned alcohol as a colorless oil (1.86 g, purity>99%, yield 100%).

NMR(¹H, 360 MHz, CDCl₃): 7.24(s, 1H); 7.18(d, J=8, 1H); 7.13(d, J=8, 1H); 3.66(d, J=6, 2H); 3.04(m, 2H); 2.71(m, 3H); 1.62(broad s, 0H) 1.31(s, 9H)δ ppm NMR(¹³C, 90.5 MHz, CDCl₃): 149.5(s); 142.5(s); 139.7(s); 124.1(d); 123.4(d); 121.5(d); 66.7(t); 41.7(d); 39.9(t); 35.3(t); 34.5(s); 31.6(3q) δ ppm MS: 204(M⁺, 21), 189(100), 171(15), 143(14), 129(16), 115 (13), 91(6), 77(3), 57(7), 41(5)

EXAMPLE 5

Preparation of 5-tert-butyl-2-methyl-2-indancarbaldehyde

To a solution of potassium tert-butoxide (Fluka, 0.45 g, 4 mmole) and of 5-tert-butyl-2-indancarbaldehyde (ex. 4; 0.71 g, 3.5 mmole), there was added at room temperature and under N₂, methyl iodide (0.56 g, 4 mmole) and reaction was allowed at room temperature, under stirring. The mixture was taken in ether and washed with NH₄Cl and brine, dried over Na₂SO₄ and concentrated (0,9 g). Chromatography on SiO₂ (30 g), with toluene as eluting agent, provided 50 mg (purity>99%, yield 7%) of the desired aldehyde.

NMR(¹H, 360 MHz, CDCl₃): 9.65(s, 1H); 7.23(s, 1H; 7.22(d, J=8, 1H);7.13(d, J=8, 1H); 3.36(d, J=16, 1H); 3.33(d, J=16, H); 2.76(d, J=16, H); 2.74(d, J=16, 1H); 1.31(s, 9H); 1.30(s, 3H)δ ppm NMR(¹³C, 90.5 MHz, CDCl₃): 204.1(d); 150.1(s); 140.8(s); 137.9(s); 124.2(d); 124.0(d); 121.6(d); 54.3(s); 41.1(t); 40.6(t); 34.6(s); 31.5(3q); 21.1(q) δ ppm MS: 216(M⁺, 37), 201(100), 183(4), 171(5), 157(16), 141 (9), 129(18), 115(5), 91(7), 71(6), 57(24), 41(8)

Odor: described above.

EXAMPLE 6

Preparation of 2-(5-tert-butyl-2-indanyl)-1,3-dioxolane

A mixture of 5-tert-butyl-2-indancarbaldehyde (ex. 4; 9.8mmole), ethyleneglycol (6.1 g, 98 mmole) and p-toluenesulfonic acid (95 mg, 0.5 mmole) in cyclohexane (25 ml), was heated to reflux (80°) during 3 h with a Dean-Stark type trap. The cooled mixture was poured on ether and aq. sat. NaHCO₃, and the organic phase was washed with aq. sat. NaHCO₃, dried over K₂CO₃ and concentrated. After bulb-to-bulb distillation, the desired dioxolane was obtained.

IR: 2980, 2890, 1500, 1400, 1370, 1275, 1210, 1155, 1130, 1080, 1050, 980, 950, 925, 830 cm⁻¹

NMR(¹H, 360 MHz, CDCl₃): 7.24(s, 1H); 7.18(d, J=8, 1H); 7.13(d, J=8, 1H); 4.87(d, J=6, 1H); 4.0(m, 2H); 3.88(m, 2H); 3.10–2.85(m, 4H); 2.71(m, 1H); 1.31(s, 9H)δ ppm NMR(¹³C, 90.5 MHz, CDCl₃): 149.5(s); 142.4(s); 139.6(s); 124.0(d); 123.4(d); 121.4(d); 106.9(d); 65.1(t); 43.0(d); 34.5(tz); 33.9(t); 31.6(3q)δ ppm MS: 246(M⁺, 16), 231(6), 184(30), 169(15), 157(9), 141(8), 128(13), 115(13), 73(100), 57(16), 45(27), 41(8), 29(9)

Odor: floral.

EXAMPLE 7

Preparation of 5-tert-butyl-1-indanacetaldehyde

Prepared in an analogous manner to that described in Example 4, via oxidation of 2-(5-tert-butyl-1-indanyl)-1-ethanol (3.85 g, 17.6 mmole) in CH₂Cl₂ (40 ml), by means of PCC (5.73 g, 25 mmole) in CH₂Cl₂ (60 ml). After the treatment described and bulb-to-bulb distillation (150°/40 Pa), there was obtained the desired carbaldehyde (2.34 g, yield 62%).

IR(neat): 2960, 2900, 2860, 2710, 1725, 1490, 1360, 1260, 830 cm⁻¹

NMR(¹H, 360 MHz, CDCl₃): 9.88(t, J=2, 1H); 7.28(s, 1H); 7.22(d, J=8, 1H);

7.08(d, J=8, 1H); 3.62(m, 1H); 2.95–2.85(m, 2H); 2.62(ddd, J₁=17, J₂=9, J₃=2, 1H); 2.43(m, 1H); 1.70(m, 1H); 1.32(s, 9H)δ ppm NMR($^{13}$C, 90.5 MHz, CDCl$_3$): 202.2(d); 150.1(s); 143.6(s); 142.5(s); 123.5(d); 122.9(d); 121.5(d); 49.5(d); 38.6(d); 34.6(s); 32.7(t); 31.6(3q); 31.5(t) δ ppm MS: 216(M$^+$, 44), 201(111), 173(79), 157(98), 143(37), 129 (72), 115(73), 102(5) 91(23), 77(10), 57(33), 41(8), 29(8)

Odor: metallic, floral.

The starting 2-(5-tert-butyl-1-indanyl)-1-ethanol was prepared from 5-tert-butyl-1-indanone [ex. 4 a)], as follows.

a) methyl 5-tert-butyl-1-indanacetate

To a suspension of sodium hydride (3.6 g of a 50% dispersion in oil, 75 mmole) previously washed with petroleum ether 30–50, in 100 ml of tetrahydrofuran (THF), there were added dropwise at 10°–20° 13.8 g (75 mmole) of trimethylphosphonoacetate in 100 ml of THF. 15 min after the end of the addition, there was added to the reaction mixture, at 11°–15°, a solution of the above-cited indanone (10.2 g, 55 mmole) in THF (150 ml). The mixture was kept under stirring for 16 h at 25°, then it was poured on 500 ml of water and extracted with ether. The combined organic extracts were washed with brine (2 times), dried (Na$_2$SO$_4$) and concentrated until forming an oil which became solid (12.6 g; isomer mixture). This product was crystallized in ether at −30°, to provide 5.56 g of methyl (E)-(5-tert-butyl-1-indanylidene)acetate.

M.p. 116.5°–117.5°

IR(CHCl$_3$): 2960, 1690, 1630, 1605, 1435, 1355, 1315, 1290, 1175, 1090, 830 cm$^{-1}$

NMR($^1$H, 360 MHz, CDCl$_3$): 7.53(d, J=8, 1H); 7.37(s, 1H); 7.30(d, J=8, 1H); 6.27(t, J=2.5, 1H); 3.76(s, 3H); 3.29(m, 2H); 3.06(t, J=6, 2H); 1.33(s, 9H) δ ppm NMR($^{13}$C, 90.5 MHz, CDCl$_3$): 168.1(s); 163.4(s); 154.8(s); 149.7(s); 137.4(s); 124.4(d); 122.2(d); 121.3(d); 106.4(d); 50.9(q); 35.0(s); 31.5(t); 31.3(3q); 30.7(t)δ ppm MS: 244(M$^+$, 43), 229(100), 213(15), 197(14), 188(9), 169 (15), 155(27), 141(25), 128(34), 115(23), 85(10), 57(13), 41(7)

A solution of this compound (7.4 g, purity 94%, 30 mmole) in ethyl acetate (150 ml) was hydrogenated in the presence of 5% Pd/C (0.68 g, 0.3 mmole) for 1 h. After filtration of the catalyst on CELITE® and concentration of the solution (7.93 g), bulb-to-bulb distillation (110°/35 Pa) provided methyl 5-tert-butyl-1-indanacetate (7.1 g, purity >99%, yield 93 % ).

IR(neat): 2970, 1735, 1435, 1360, 1270, 1190, 1170, 830 cm$^{-1}$

NMR($^1$H, 360 MHz, CDCl$_3$): 7.26(s, 1H); 7.20(d, J=8, 1H); 7.00(d, J=8, 1H); 3.72(s, 3H); 3.55(m, 1H); 3.0–2.7(m, 3H); 2.5–2.3(m, 2H); 1.73(m, 1H); 1.32(s, 9H)δ ppm NMR($^{13}$C, 90.5 MHz, CDCl$_3$): 173.3(s); 149.9(s); 143.7(s); 142.7(s); 123.4(d); 122.9(d); 121.5(d); 51.5(q); 41.0(d); 39.7(t); 34.5(s); 32.7(t); 31.6(3q); 31.3(t)δ ppm MS: 246(M$^+$, 28), 231(58), 189(52), 173(74), 157(65), 143 (32), 129(100), 115(54), 91(15), 77(7), 57(31), 41(7)

b) 2-(5-tert-butyl-1-indanyl)-1-ethanol

Prepared from the ester described under a) (6.3 g, 25 mmole), in an analogous manner to that described in ex. 4 c), by means of LiAlH$_4$ (38 mmole). There were added 2 ml of ethyl acetate to the reaction mixture, then 4.85 ml of aq. 1N NaOH and the mixture was stirred for 30 min at room temperature. After addition of Na$_2$SO$_4$ and filtration, it was washed with ether and evaporated (5.5 g). Bulb-to-bulb distillation (115°/30 Pa) provided the desired alcohol (5.5 g, purity>99%, yield 99%).

IR(neat): 3320, 2960, 2860, 1490, 1360, 1265, 1060, 1025, 825 cm$^{-1}$

NMR($^1$H, 360 MHz, CDCl$_3$): 7.27(s, 1H); 7.21(d, J=8, 1H); 7.14(d, J=8,1 H); 3.81(m, 2H); 3.2(m, 2H); 3.0–2.8(m, 2H); 2.32(m, 1H); 21.5(m, 1H); 1.70(m, 2H); 1.32(s, 9H)δ ppm NMR($^{13}$C, 90.5 MHz, CDCl$_3$): 149.6(s); 144.0(s); 143.7(s); 123.2(d); 123.0(d); 121.4(d); 61.7(t); 41.1(d); 38.0(t); 34.5(s); 32.5(t); 31.6(3q) δ ppm MS: 218(M$^+$, 56), 203(99), 200(3), 185(25), 173(100), 161 (34), 143(30), 128(22), 115(20), 91 (8), 77(4), 57(25), 41 (6), 31 (9)

EXAMPLE 8

Preparation of 3-(3-tert-butyl-5-methylphenyl)propanal

To 1.2 g (5.7 mmole) of (E)-3-(3-tert-butyl-5-methylphenyl)-2-propenal in ethanol (20 ml) there were added 5% Pd/C (0.12 g) and sodium acetate (0.12 g, 1.4 mmole). The mixture was hydrogenated at room temperature and atmospheric pressure during 6 h. After filtration of the catalyst, the solvent was evaporated (1.2 g). The raw product was dissolved in CH$_2$Cl$_2$ (20 ml) and a suspension of PCC (0.62 g, 2.8 ml) in CH$_2$Cl$_2$ (20 ml) was added thereto at room temperature. After 2 h, the mixture was diluted in ether (100 ml) filtered on a FLORISIL® column (Fluka) and concentrated (1.2 g). Bulb-to-bulb distillation (80°/10 Pa) provided 3-(3-tert-butyl-5-methylphenyl)propanal (6.88 g, purity>95%, yield 70%).

IR(neat): 2960, 2860, 1720, 1595, 1470, 1360, 1220, 860, 710 cm$^{-1}$

NMR($^1$H, 360 MHz, CDCl$_3$): 9.82(t, J=1.5, 1H); 7.06(s, 1H); 7.02(s, 1 H); 6.83(s, 1H); 2.92(t, J=8, 2H); 2.76(dt, J$_1$=1.5, J$_2$=8, 2H); 2.32(s, 3H); 1.30(s, 9H) δ ppm NMR ($^{13}$C, 90.5 MHz, CDCl$_3$): 201.8(d); 151.5(s); 139.9(s); 137.5(s); 126.2(d); 124.2(d); 122.4(d); 45.5(t); 34.5(s); 31.4(3q); 28.3(t); 21.6(q)δ ppm MS: 204(M$^+$, 33), 189(42), 161(49), 145(100), 133(25), 119(23), 105(20), 91(18), 77(9), 65(4), 57(18), 41(6), 29(5)

Odor: described above.

The starting unsaturated aldehyde was prepared according to Scheme II, as follows.

5-Tert-butyl-1,3-dimethylbenzene (Fluka, 190 g, 1.17 mole) was electrochemically oxidized (anode: graphite; cathode: inox; current density: 30 mA/cm$^2$; 4 F/mole) at a temperature of about 35° in solution in methanol, using sodium p-toluenesulfonate as electrolyte. After distillation (Vigreux), there were obtained 77.3 g of 1-tert-butyl-3-(dimethoxy-methyl)-5-methylbenzene, having a purity of 87% (yield 26%). B. p. 118°–128°/11×10$^2$ Pa IR(neat): 2980, 2920, 2840, 1745, 1605, 1455, 1370, 1235, 1200, 1175, 1120, 1090, 1070, 1000, 920, 870, 715 cm$^{-1}$ NMR($^1$H, 360 MHz, CDCl$_3$): 7.25(s, 1H); 7.17(s, 1H); 7.08(s, 1H); 5.35(s, 1H); 3.34(s, 6H); 2.35(s, 3H); 1.32(s, 9H)δ ppm NMR($^{13}$C, 90.5 MHz, CDCl$_3$): 151.2(s); 137.7(s); 137.4(s); 126.3(d); 124.5(d); 120.7(d); 103.9(d); 52.9(2q); 34.6(s); 31.4(3q); 21.6(q)δ ppm MS: 222(M$^+$, 2), 207(3), 191(100), 177(5), 161(9), 133 (9), 115(6), 105(8), 91(8), 75(10), 57(3), 41(2)

To the thus obtained acetal (12.7 g, 50 mmole) there was added, at −10°, quickly and under stirring, a solution of ZnCl$_2$ (0.27 g, 2 mmole) in ethyl acetate (2.7 ml). After 5 min, 85% H$_3$PO$_4$ was added (0.24 ml, 3.5 mmole). After 15 min, ethylvinylether was added dropwise (Fluka purum, 7.3 ml, 75 mmole) while maintaining the temperature between −10 and 0°. After 2.5 h at 0° and 15 h at room temperature, chromatographic analysis indicated the formation of 65% of the intermediate acetais. This raw mixture of acetais was added by means of a cannula to a mixture of formic acid (12.5 ml), sodium formate (4 g) and water (6.5 ml), and the whole was heated to 110° with a bath, while continuously distilling the volatiles (b. p. 80°–90°/106 Pa), for 1 h. The residue was diluted in water (40 ml) and petroleum ether 30°–50° (40 ml) for extraction. The organic phase was washed, dried and concentrated. The raw product (12.1 g, purity 66%, yield 79%) was distilled on a Vigreux column (5 cm) to provide (E)-3-(3-tert-butyl-5-methylphenyl)-2-propenal (6.4 g).

B.p. 70°–82°/10 Pa.

IR(neat): 2960, 2860, 1670, 1620, 1590, 1475, 1360, 1240, 1125, 970, 700 cm$^{-1}$ NMR(1H, 360 MHz, CDCl$_3$): 9.69(d, J=8, 1H); 7.46(d, J=15, 1H); 7.38(s, 1H); 7.29(s, 1H); 7.22(s, 1H); 6.72(dd, J$_1$=16, J$_2$=8, 1H); 2.38(s, 3H); 1.3(s, 9H) δ ppm NMR($^{13}$C, 90.5 MHz, CDCl$_3$): 193.8(d); 157.7(d); 152.1(s); 138.4(s); 133.7(s); 129.5(d); 128.2(d); 126.2(d); 123.1 (d); 34.6(s); 31.2(3q); 21.5(q)δ ppm MS: 202(M$^+$, 12), 187(25), 159(13), 145(100), 128(12), 115 (16), 105(4), 91(8), 79(4), 65(3), 55(3), 41 (3)

EXAMPLE 9

Preparation of 3-(3-tert-butyl-5-methylphenyl)-2-methylpropanal

Prepared by hydrogenation of 3-(3-tert-butyl-5-methylphenyl)-2-methyl-2-propenal (2,32 g, 8,5 mmole), in a similar manner to that described in Example 8 (reaction 2.5 h). After the treatment described and bulb-to-bulb distillation (90°–105°/10 Pa), there were obtained 1.5 g of product having a purity of 86% (yield 78%). Purification on a SiO$_2$ column, with CH$_2$Cl$_2$ as eluting agent, provided the desired propanal 94% pure.

IR(neat): 2970, 2870, 1725, 1600, 1475, 1450, 1360, 1225, 860, 715 cm$^{-1}$

NMR($^1$H, 360 MHz, CDCl$_3$): 9.72(d, J=2, 1H); 7.05(s, 1H); 6.98(s, 1H); 6.80 (s, 1H); 3.04(dd, J$_1$=13, J$_2$=6, 1H); 2.64(m, 1H); 2.56(dd, J$_1$=13, J$_2$=8, 1H); 2.32(s, 3H);1.30(s, 9H); 1.08(d, J=7, 3H)δ ppm NMR($^{13}$C, 90.5 MHz, CDCl$_3$): 204.6(d); 151.4(s);138.4(s); 137.6(s); 126.9(d); 124.2(d);123.2(d);48.1(d);36.9(t);34.5(s);31.4(3q);21.6(q); 13.3(q) δ ppm MS:218(M$^+$, 32),203(20), 190(11), 175(100), 161(35), 145 (80), 133(57), 115(28), 105(45), 91(28), 77(14), 57(32), 41(22), 29(21)

Odor: described above.

The starting unsaturated aldehyde was prepared from 1-tert-butyl- 3-(dimethoxymethyl)-5-methylbenzene (see ex. 8), according to scheme II, as follows.

To a solution of the above-mentioned acetal (22.2 g, 90 mmole) in THF (50 ml), there was added 10% aq. HCl (10 ml) and the mixture was stirred during 1.5 h. After the usual treatment and distillation under vacuum (10$^3$ Pa), 2 fractions were obtained, of which the purest (11.2 g) contained 3-tert-butyl-5-methylbenzenaldehyde 95 % pure.

B. p. 112°–114°/10$^3$ Pa

IR(neat): 2980, 2880, 1700, 1600, 1480, 1370, 1305, 1235, 1170, 1160, 875, 710 cm$^{-1}$ NMR($^1$H, 360 MHz, CDCl$_3$): 9.98(s, 1H); 7.71(s, 1H); 7.50(s, 1H); 7.47(s, 1H); 2.43(s, 3H); 1.35(s, 9H) δ ppm NMR($^{13}$C, 90.5 MHz, CDCl$_3$): 192.9(d); 152.2(s); 138.5(s); 136.5(s); 132.6(d); 127.8(d); 123.9(d); 34.7(s); 31.2(3q); 21.4(q) δ ppm MS: 176(M$^+$, 26), 161(100), 145(2), 133(31), 115(16), 105 (32), 51(5), 41(11), 29(7)

To a solution of this benzaldehyde (3.55 g, 18 mmole) in methanol (20 ml), there was added K$_2$CO$_3$ (2.76 g, 20 mmole) and the mixture was heated to reflux (65° ). A solution of propanal (1.71 g, 24 mmole) in methanol (5 ml) was added dropwise, during 1 h. After having heated to reflux for yet 1 h, the mixture was cooled and diluted in ether, washed with aq. sat. NaHCO$_3$ and brine, dried over Na2SO$_4$ and concentrated (3.75 g). After bulb-to-bulb distillation (125°/10 Pa), there was obtained 3-(3-tert-butyl-5-methylphenyl)-2-methyl-2-propenal as a colorless oil (1.83 g, purity 79%, yield 57%).

IR(neat): 2970, 2930, 2870, 1675, 1622, 1595, 1480, 1445, 1400, 1365, 1280, 1230, 1195, 1030, 920, 835, 705 cm$^{-1}$ NMR($^1$H, 360 MHz, CDCl$_3$): 9.58(s, 1H); 7.35(s, 1H); 7.25(s, 1H); 7.18(s, 1); 2.40(s, 3H); 2.09(s, 3H); 1.35(s, 9H) δ ppm NMR($^{13}$C, 90.5 MHz, CDCl$_3$): 195.7(d); 151.6(s); 150.8(s); 138.0(2s); 134.9(s); 127.8(d); 127.7(d); 124.5(d); 34.6(s); 31.3(3q); 21.7(q); 11.0(q) δ ppm MS: 216(M$^+$, 8), 201(20), 173(18), 159(100), 145(8), 131(19), 105(7), 91(7), 77(4), 57(3), 41(3), 29(2)

EXAMPLE 10

Preparation of 3-(3,3-dimethyl-5-indanyl)propanal and 3-(1, 1-dimethyl-5-indanyl)propanal Prepared by hydrolysis of (E)-3-(3,3-dimethyl-5-indanyl)-1-propenyl acetate [1.93 g, 7.4 mmole; mixture containing 58% of this compound and 25% of its (1,1-dimethyl-5-indanyl) isomer] by means of H$_2$SO$_4$ (24 ml) in an analogous manner to that described in Example 1. After bulb-to-bulb distillation (100°/11 Pa), there was obtained a colorless oil (1.43 g, yield 90%, purity 95%) containing 58% of 3-(3,3-dimethyl-5-indanyl)propanal and 28% of 3-(1,1-dimethyl-5-indanyl)propanal.

IR(neat): 2960, 2860, 2720, 1728, 1490, 1450, 1360, 825 cm$^{-1}$ 3-(3,3-Dimethyl-5-indanyl)propanal presented the following analytical characters:

NMR($^1$H, 360 MHz, CDCl$_3$): 9.82(t, J=15, 1H); 7.10(d, J=8, 1H); 6.96(d, J=8, 1H); 6.95(s, 1H); 2.94(t, J=7,2H); 2.84(t, J=7,2H); 2.75(t, J=7,2H); 1.91(t, J=7,2H); 1.24(s, 6H) δ ppm NMR($^{13}$C, 90.5 MHz, CDCl$_3$): 201.8(d); 153.1(s); 140.8(s); 138.4(s); 126.2(d); 124.5(d); 121.9(d); 45.6(0; 43.9(s); 41.6(0; 29.6(t); 28.6(2q); 28.2(t) δ ppm MS: 202(M$^+$, 22), 187(100), 159(4), 143(74), 128(40), 115(21), 91(9), 77(6), 63(3), 51(3),39(4),29(9)

Odor: described above.

The starting acetate was prepared from 1,1-dimethylindane [5.2 g, 35 mmole; this compound is prepared via known methods; see, for example, M.T. Bogert and al., J. Amer. Chem. Soc. 56, 185 (1934); S.T. Bright and al., J. Org. Chem. 55, 1338 (1990) and ref. there-cited] by reacting with 1,1-dimethylindane acrolein diacetylacetal (7.9ml, 52mmole), in the presence of TiC$_{14}$ (5.8 ml, 52 mmole) and of BF$_3$O(C$_2$HS)$_2$ (0.25 ml, 1 mmole), in an analogous manner to that described in Example 1. After purification by chromatography (SiO$_2$, cyclohexane/ether 9:1) and bulb-to-bulb distillation (120°/10 Pa), there was obtained a colorless oil (2.94 g, yield 32%, purity 93%) consisting of a mixture of (E)-3-(3,3-dimethyl-5-indanyl)-1-propenyl acetate (58%) and of (E)-3-(1,1-dimethyl-5-indanyl)-1-propenyl acetate (25%).

IR(neat): 2960, 2860, 1755, 1665, 1370, 1225, 1100, 935, 900 cm$^{-1}$

The above-mentioned major isomer presented the following analytical characters:

NMR($^1$H, 360 MHz, CDCl$_3$): 7.18(dt, J$_1$=12, J$_2$=1.5, 1H); 7.10 (d, J=8, 1H) 6.96(d, J=8, 1H); 6.95(s, 1H); 5.58(dt, $J_1=12$, $J_2=7$, 1H); 3.32(d, J=7,2H); 2.84(t, J=7, 2H); 2.11 (s, 3H); 1.91 (t, J=7, 2H); 1.25(s, 6H) δ ppm NMR($^{13}$C, 90.5 MHz, CDCl$_3$): 168.1(s); 153.0(s); 140.8(s); 137.8(s); 136.1(d); 126.3(d); 124.4(d); 121.9(d); 114.2(d); 43.9(s); 41.6(0; 33.6(t); 29.6(t); 28.6(2q); 20.7(q) δ ppm MS: 244(M$^+$, 32), 229(25), 202(21), 187(100), 169(8), 157(7), 146(19), 131(30), 115(30), 91(14), 77(5), 57(9), 43(64)

EXAMPLE 11

Preparation of 3-(1,1-dimethyl-5-indanyl)-2-methylpropanal and 3-( 3,3-dimethyl-5-indanyl)-2-methylpropanal Prepared by hydrolysis of (E)-3-(1,1-dimethyl-5-indanyl)-2-methyl- 1-propenyl acetate [2 g, 7 mmole; mixture 51% of this compound and 33% of its 3,3-dimethyl-5-indanyl isomer] in methanol (20 ml), by means of K$_2$CO$_3$ (0.1 g, 0.7 mmole). After bulb-to-bulb distillation (100°/10 Pa), there was obtained a colorless oil (1.33 g, yield 84%, purity 95%) containing 59% of 3-(1,1-dimethyl-5-indanyl)-2-methylpropanal and 31% of 3-(3,3-dimethyl- 5-indanyl)-2-methylpropanal.

IR(neat): 2960, 2860, 2710, 1725, 1490, 1455, 1360, 1125, 835 cm$^{-1}$ 3-(1,1-Dimethyl-5-indanyl)-2-methylpropanal presented the following analytical characters:

NMR($^1$H, 360 MHz, CDCl$_3$): 9.72(d, J=1.5, 1H); 7.04(d, J=7.5, 1H); 6.99(s, 1H); 6.96(d, J=7.5, 1H); 3.04(dd, $J_1$=13, $J_2$=6, 1H); 2.84(t, J=7, 2H); 2.63(m,1H); 2.57(dd, $J_1$=13, $J_2$=8, 1H); 1.91(t, J=7, 2H); 1.24(s, 6H); 1.09(d,J=7,3H); δ ppm NMR($^{13}$C, 90.5 MHz, CDCl$_3$): 204.7(d); 150.8(s); 143.2(s); 136.7(s); 127.1(d); 125.1(d); 121.9(d); 48.2(d); 43.6(s); 41.5(0; 36.6(t); 30.0(t); 28.6(2q); 13.3(q) δ ppm MS: 216(M$^{+}$18), 201(100), 173(3), 159(15), 143(54), 128(33), 115(17), 91(8), 77(5), 51 (3), 39(4), 29(9)

Odor: described above.

The starting acetate was prepared in an analogous manner to that described in the preceding example, starting from 1,1-dimethylindane (4.75 g, 32 mmole, purity 98%), by means of TiCl$_4$ (3.5 ml, 32 mmole), BF$_3$.O(C$_2$HS)$_2$(0.25 ml, 1 mmole) and of methacrolein diacetylacetal (5.4 ml, 32 mmole). Bulb-to-bulb distillation provided a colorless oil (6 g, purity 65%) containing 40% of (E)-3-(1,1-dimethyl-5-indanyl)-2-methyl-1-propenyl acetate and 22% of (E)-3-(3, 3-dimethyl-5-indanyl)-2-methyl-1-propenyl acetate.

IR(neat): 2950, 2855, 1750, 1680, 1480, 1435, 1380, 1365, 1225, 1100, 920, 810 cm$^{-1}$ The major isomer presented the following analytical characters:

NMR($^1$H, 360 MHz, CDCl$_3$): 7.05(s, 1H); 7.03(d, J=7.5, 1H); 7.00(s, 1H; 6.98 (d,J=7.5, 1H); 3.22(s, 2H); 2.84(t, J=7, 2H); 2.13(s, 3H); 1.91 (t, J=7, 2H); 1.61(s, 3H); 1.23(s, 6H) δ ppm NMR($^{13}$C, 90.5 MHz, CDCl$_3$): 168.3(s); 150.7(s); 143.0(s); 136.9(s); 131.1(d); 126.9(d); 124.8(d); 121.8(d); 121.6(s); 43.6(s); 41.5(t); 40.2(t); 29.9(t); 28.7(2q); 20.8(q); 13.6(q) δ ppm MS: 258(M$^{+}$12), 243(6), 216(27), 201(100), 183(4), 171(3), 143(10), 131(37), 115(11), 91(8), 71(5), 43(21)

EXAMPLE 12

Preparation of 6-tert-butyl-1-indanacetaldehyde
Prepared in an analogous manner to that described in Example 4, by oxidizing 2-(6-tert-butyl-1-indanyl)-1-ethanol (8.53 g, 32.1 mmole, 82.3% pure) in dichloromethane (50 ml), by means of PCC (Fluka, 15.0 g, 68 mmole) in dichloromethane (100 ml). After the treatment described and bulb-to-bulb distillation (120°/15Pa), there was obtained the above-mentioned compound with a purity of 84% (6.01 g, yield 72.7%). Further purification by chromatography provided the desired compound 98% pure, presenting the following analytical characters:

IR(neat): 2980, 2880, 2620, 1730, 1495, 1370, 1270, 1125, 830 cm$^{-1}$

NMR($^1$H, 360 MHz, CDCl$_3$) :9.88(s, CHO); 7.22(d, J=8, 1H); 7.19(s, 1H); 7.17(d, J=8, 1H); 3.60–3.67(m, 1H); 2.80–2.96(m, 3H); 2.57–2.66(m, 1H); 2.37–2.46(m, 1H; 1.65–1.75(m, 1H); 1.29(s, 9H) δ ppm NMR($^{13}$C, 90.5 MHz, CDCl$_3$): 202.0(d); 149.7(s); 145.3(s); 140.8(s); 124.2(d); 124.0(d); 120.2(d); 49.6(t); 39.1(d); 34.6(s); 32.7(t); 31.6(3q); 30.9(t) δ ppm MS:216(16), 201(42), 172(45), 159(27), 157(100), 141(21), 131(25),129(61), 117(33), 115(51), 91(16), 77(6), 57(11)

Odor: described above.

The starting 2-(6-tert-butyl-1-indanyl)-1-ethanol is prepared from 3-( 4-tert-butyl-1-phenyl)propanal, as follows:

a. 6-tert-butyl-1-1-indanone

In a 500 ml flask, 20 g of the above-mentioned propanal 92.2% pure (96.9 mmole) are dissolved in 100 ml of acetone Fluka puriss, then 55.4 ml of 2.1M Jones reactant are added dropwise (116.3 mmole; 1.2 eq) while keeping the rection temperature<30° with an ice water bath. After 16 h at room temperature, 10 ml of isopropanol are added and the solvent is evaporated. Extract with ether, wash with brine until neutral pH and concentrate under vacuum. There were obtained 21.1 g of 3-( 4-tert-butylphenyl)propanoic add in the form of pale green crystals, with a GC purity of 90% and the following analytical characters:

M.p.: 147.5°–148° C.

IR(CHCl$_3$): 2960 (broad), 2640, 1710, 1410, 1270, 835 cm$^{-1}$

NMR($^1$H, 360 MHz, CDCl$_3$): 11.9–11.6(broad, COOH); 7.32(d, J=8 Hz, 2H; 7.14(d, J=8 Hz, 2H); 2.93(t, J=8 Hz, 2H); 2.68(t, J=8 Hz, 2H); 1.3(s, 9H); δ ppm NMR($^{13}$C, 90.5 MHz, CDCl$_3$): 179.6(s); 149.2(s); 137.1(s); 127.9(2d); 125.5(2d); 35.6(t); 34.4(s); 31.4(3q); 30.0(t) δ ppm

MS :206(13), 191(100), 163(5), 145(11), 131(56), 117(27), 91 (19),77(7), 45(7)

In a 500 ml flask there were suspended 21.1 g of the above-mentioned acid (92.1 mmole) in 10.6 ml of thionyl chloride (Fluka purum 99%, 144.7 mmole) then the mixture was heated to 60° and stirred at this temperature until all the acid had dissolved (~45 min). Evaporate the excess of thionyl chloride with water pump vacuum, then bulb-to-bulb distill (150°/30 Pa). There were obtained 12.88 g of the acid chloride. In a 250 ml sulfuration flask there were dissolved 11.88 g of this chloride (~52.9 mmole) in 100 ml of CH$_2$Cl$_2$ puriss, then the solution was cooled with an ice bath and 8.5 g of aluminium chloride (63 mmole) were added in small portions. After 2 h of stirring at 0°, the reaction mixture is poured on a mixture of ice and ether. The product is extracted with ether, washed with brine, then concentrated under vacuum. There were obtained 10.3 g of raw product containing 86% of 6-tert-butyl-1-indanone and 6.1% of 6-tert-butyl-3-indanone. Bulb-to-bulb distillation of this raw product (120°/20 Pa) provided 8.97 g of 95% pure product, containing 89.3% of 6-tert-butyl-1-indanone.

IR(CHCl$_3$): 2960, 1700, 1610, 1490, 1290, 840 cm$^{-1}$

NMR($^1$H, 360 MHz, CDCl$_3$): 7.78(d, J=2 Hz, 1H); 7.66(dd, J=8,2 Hz, 1H); 7.49(d, J=8 Hz, 1H); 3.09(t, J=6 Hz, 2H); 2.68(t, J=6 Hz, 2H); 1.33 (s,9H) δ ppm NMR($^{13}$C, 90.5 MHz, CDCl$_3$): 207.4(s); 152.6(s); 150.8(s); 137.0(s); 132.5(d); 126.3(d); 120.0(d); 36.7(0; 34.8(s); 31.4(3q); 25.33(t) δ ppm

MS: 188(24), 173(100), 145(21), 131(30), 128(9), 115(10), 91(6), 77(4)

Odor: metallic, dusty, motor oil.

b. methyl(E)-(6-tert-butyl-1-indanylidene) acetate

In a 250 ml three-neck flask, dissolve 8.52 g of 6otert-butyl-1-indanone (45.3 mmole) in 100 ml of pentane. Then add quickly 10.1 ml of trimethylphosphonoacetate (68 mmole; 1.5 eq), then dropwise 11.7 ml of sodium methylate (Fluka, 5.4 M in methanol; 63.4 mmole; 1.4 eq) and stirr at room temperature during 24 h. The reaction mixture is poured on a mixture of ether and sat. aq. NaHCO$_3$, extracted with ether, washed with brine, then concentrated under vacuum to provide 10.7 g of a mixture containing 18.9% of methyl 5-tert-butyl-3(1H)-indenacetate, 4.2% of methyl (Z)-(6-tert-butyl-1-indanylidene)acetate and 53.2% of methyl (E)-(6-tert-butyl-1-indanylidene) acetate. This raw product was used in the following step.

IR(neat): 2980, 1740, 1710, 1680, 1450, 1355, 1200, 1170, 860, 835 cm$^{-1}$

Major isomer:

NMR($^1$H, 360 MHz, CDCl$_3$): 7.61(d, J=2 Hz, 1H); 7.42(dd, J=8, 2 Hz, 1H); 7.28(d, J=8 Hz, 1H); 6.33(t, J=2 Hz, 1H); 3.76(s, 3H); 3.28–3.34(m, 2H); 3.03(t, J=6 Hz, 2H); 1.34(s, 9H) δ ppm MS:244(47), 229(100), 213(19), 197(41), 188(43), 169(17), 155(30) 141(21) 129(38), 115(16), 85(15), 57(11)

c. methyl 6-tert-butyl-1-indanacetate

The hydrogenation of 10.7 g (76.3%; 33.4 mmole) of the mixture of esters precedingly described was carried out in solution in ethyl acetate (100 ml) in the presence of 2.25 g of 5% Pd on carbon. The suspension was stirred during 17 h under hydrogen atmosphere and provided, after filtration of the catalyst and concentration, 10.7 g of raw methyl 6-tert-butyl-1-indanacetate with a purity of 80.5%. The raw product was used in the following step.

IR(neat): 2990, 2940, 1740, 1500, 1440, 1370, 1270, 1180, 830 cm$^{-1}$

NMR($^1$H, 360 MHz, CDCl$_3$): 7.14–7.23(m, 3H); 3.72(s, 3H); 3.53–3.62(m, 1H); 2.76–2.94(m, 3H); 2.33–2.48(m, 2H); 2.70–2.80(m, 1H); 1.3(s, 9H) δ ppm NMR($^{13}$C, 90.5 MHz, CDCl$_3$): 173.31(s); 149.48(s); 145.45(s); 140.88(s); 124.08(d); 123.94(d); 120.25(d); 51.53(q); 41.51(d); 39.85(t); 34.60(s); 32.62(t); 31.58(q); 30.67(t) δ ppm MS: 246(27), 231(59), 189(41), 173(31), 157(100), 129(70), 115 (29), 91(8), 57(15)

d. 2-(6-tert-butyl-1-indanyl)-1-ethanol

To a suspension of 1.72 g of LiAlH$_4$ (45.03 mmole) in 100 ml of ether was added dropwise a solution of 10.7 g of methyl 6-tert-butyl-1-indanacetate (36.9 mmole) dissolved in 50 ml of ether. After refluxing the suspension during 2 h, 8.6 ml of 1N NaOH were carefully added and, after 1 h, the suspension was filtered and concentrated to give 9.05 g of raw 2-( 6-tert-butyl-1-indanyl)-1-ethanol 78.1% pure. Bulb-to-bulb distillation (150°/20 Pa) provided 8.53 g of 2-(6-tert-butyl-1-indanyl)-1-ethanol with a GC purity of 82.3%. Yield of the last three steps: 71.0%.

IR(neat): 3320, 2960, 2860, 1480, 1355, 1255, 1150, 820 cm$^{-1}$

NMR($^1$H, 360 MHz, CDCl$_3$): 7.24(d, J=1Hz, 1H); 7.21(dd, J=8, 1, 1H); 7.15(d, J=8 Hz, 1H); 3.76–3.84(m, 2H); 3.17–3.27(m, 1H); 2.75–2.94(m, 2H); 2.26–2.36(m, 1H); 2.12–2.21(m, 1H); 1.64–1.76(m, 2H); 1.40–1.44(broad, OH); 1.32(s, 9H) δ ppm NMR($^{13}$C, 90.5 MHz, CDCl$_3$): 149.3(s); 146.8(s); 140.9(s); 124.0(s); 123.5(d); 120.4(d); 61.6(t); 41.6(d); 38.0(0; 34.6(s); 32.5(t); 31.6(3q); 30.9(t) δ ppm MS: 218(60), 203(100), 185(29), 173(84), 161(84), 157(52), 143 (84), 129(60), 117(70), 91(22), 77(10), 57(50)

EXAMPLE 13

Preparation of 3-(5-indanyl)-1-propanal and 3-(4-indanyl)-1-propanal

Prepared by hydrolysis of (E)-3-(5-indanyl)-1-propenyl acetate [3.3 g; 13.6 mmole; 89% pure mixture containing 74% of this compound and 15% of (E)-3-(4-indanyl)-1-propenyl acetate], by means of 25% sulfuric acid (6 ml) in THF (25 ml), in an analogous manner to that described in Example 1. After 4 h of reflux and the treatment described, bulb-to-bulb distillation (125°/10 Pa) provided 2.07 g of a product having a purity of 99% and containing 83% of 3-(5-indanyl)-1-propanal and 16% of 3-(4-indanyl)-1propanal (yield 87%).

Analytical characters:

IR(neat): 2950, 2840, 2710, 1720, 1490, 1435, 1060, 820 cm$^{-1}$

Major isomer:

NMR($^1$H, 360 MHz, CDCl$_3$): 9.78(d, J=1.5 Hz, CHO); 7.13(d, J=8 Hz, 1H); 7.05(s, 1H); 6.94(d, J=8 Hz, 1H); 2.91(t, J=8 Hz, 2H); 2.87(t, J=7 Hz, 2H); 2.86(t, J=7 Hz, 2H); 2.73(dt, J=1.5, 8 Hz, 2H); 2.05(quint, J=7 Hz, 2H) δ ppm NMR$^{13}$C, 90.5 MHz, CDCl$_3$): 201.8(s); 144.7(s); 142.2(s); 138.1(s); 126.1(d); 124.4(d); 124.3(d); 45.6(0; 32.8(0; 32.4(0; 28.0(0; 25.5(t) δ ppm MS: 174(73), 156(3), 145(14), 131(76), 128(33), 118(100), 103 (7), 91(37), 77(12), 65(8), 63(9), 51(9), 39(10), 29(14)

Odor: described above.

The starting acetate was prepared thus:

In a 200 ml three-neck flask, 6.4 g of indane (Fluka purum 95%, 50 mmole) are dissolved in 50 ml of CH$_2$Cl$_2$ puriss, then add dropwise and quickly at room temperature 6.0 ml of TiCl$_4$ (Fluka, 55 mmole; 1.1 eq) then 0.12 ml of BF3.Et$_2$O (Fluka 48%, 1 mmole; 0.02 eq). After stirring at room temperature during 30 min, the solution is cooled to −10°, then a solution of 7.9 g of acrolein diacetylacetal (Fluka 98%, 50 mmole) dissolved in 20 ml of CH$_2$Cl$_2$ is added thereto dropwise in 30 min. After stirring the solution during 1 h at −5°, the reaction mixture is poured on a mixture of ice and 10% HCl$_1$, then extracted with ether. The ether phase is then washed with brine until neutral pH, then dried over Na$_2$SO$_4$ and concentrated under vacuum. There were obtained 10.9 g of a brown liquid which was bulb-to-bulb distilled (185°/10 Pa) to provide 4.51 g of a product containing 74.0% of (E)- 3-(5-indanyl)-1-propenyl acetate and 15.0% of (E)-3-(4-indanyl)-1-propenyl acetate (yield 37,0%).

IR(neat): 2960, 2840, 1755, 1670, 1430, 1370, 1225, 1100, 940, 900 cm$^{-1}$

The following data are for the major isomer:

NMR($^1$H, 360 MHz, CDCl$_3$): 7.17(dt, J=12, 1 Hz, 1H); 7.13(d, J=7 Hz, 1H); 7.05(s, 1H); 6.95(d, J=7 Hz, 1H); 5.57(dt, J=12, 8 Hz, 1H); 3.28(d, J=8 Hz, 2H); 2.86(t, J=7 Hz, 4H); 2.1 (s, 3H); 2.05(m, 2H) δ ppm NMR($^{13}$C, 90.5 MHz, CDCl$_3$): 168.2(s); 144.6(s); 142.2(s); 137.5(s); 136.1(s); 126.2(d); 124.3(2d); 114.2(d); 33.4(t); 32.8(t); 32.5(t); 25.5(t); 20.7(q) δ ppm MS: 216(47), 174(65), 156(15), 145(28), 131(44), 118(89), 91 (22), 77(7), 63(7), 55(7), 43(100), 39(7)

EXAMPLE 14

Preparation of 3-(5-indanyl)-2-methyl-1-propanal

Prepared by hydrolysis of (E)-3-(5-indanyl)-2-methyl-1-propenyl acetate [4 g, 17.4 mmole; 96% pure mixture containing 84.1% of this compound and 11.7% of (E)-3-(4-indanyl)-2-methyl-1-propenyl acetate], by means of 10 ml of 25% sulfuric acid and in 50 ml of THF, in an analogous manner to that described in the previous example. After treatment and bulb-to-bulb distillation (110°/15 Pa) there were obtained 2.81 g of a 96% pure product, containing 3-(5-indanyl)-2-methyl-1-propanal and 3-(4-indanyl)-2-methyl-1-propanal in a 9:1 ratio (yield 82.4%).

Analytical characters:

IR(neat): 2940, 2860, 2700, 1750, 1500, 1450, 915, 835, 800 cm$^{-1}$

Major isomer:

NMR($^1$H, 360 MHz, CDCl$_3$): 9.71(d, J=2 Hz, CHO); 7.13(d, J=8 Hz, 1H); 7.03(s, 1H); 6.93(d, J=8 Hz, 1H); 3.03(dd, J=13, 5 Hz, 1H); 2.86(t, J=7.5 Hz, 4H); 2.63(m, 1H); 2.57(dd, J=13, 8 Hz, 1H); 2.05(quint, J=7.5 Hz, 2H); 1.08(d, J=8 Hz, 3H) δ ppm NMR($^{13}$C, 90.5 MHz, CDCl$_3$): 204.6(d); 144.6(s); 142.3(s); 136.5(s); 126.8(d); 125.0(d); 124.3(d); 48.3(d); 36.6(0; 32.8(0; 32.5(0; 25.5(0; 13.3(q) δ ppm MS: 188(31), 173(2), 160(4), 145(5), 131(100), 128(15), 118 (15), 118(28), 115(24), 91(20), 77(6), 29(8)

Odor: citrus, metallic, citronellal.

The starting acetal is prepared thus:

In a 200 ml three-neck flask, 6.5 ml of indane (Fluka purum 95%, 50 mmole) are dissolved in 40 ml of CH$_2$Cl$_2$ puriss, then add dropwise and quickly at room temperature 6.0 ml of TIC14 (Fluka, 55 mmole; 1.1 eq) then 0.39 ml of BF3.Et20 (Fluka 48%, 1.5 mmole; 0.03 eq). After stirring at room temperature during 30 min, the solution is cooled to −10°, then a solution of 9.22 ml of methacrolein diacetylacetal (Fluka 98%, 50 mmole) dissolved in 25 ml of CH$_2$Cl$_2$ is added thereto dropwise in 30 min. After stirring the solution during 1 h at −5°, the reaction mixture is poured on a mixture of ice and 10% HCl, then extracted with ether. The ether phase is then washed with brine until neutral pH, then dried over Na$_2$SO$_4$ and concentrated under vacuum. There were obtained 11.2 g of a brown liquid which was bulb-to-bulb distilled (140°/15 Pa) to provide 4.18 g of a product containing 84.1% of (E)-3-(5-indanyl)-2-methyl-1-propenyl acetate and 11.7% of (E)-3-( 4-indanyl)-2-methyl-1-propenyl acetate (yield 34.7%).

IR(neat): 2942, 1752, 1490, 1369, 1228, 1099, 921,813 cm$^{-1}$

Major isomer:

NMR($^1$H, 360 MHz, CDCl$_3$): 7.13(d, J=8 Hz, 1H); 7.04(s, 2H); 6.94(d, J=8 Hz 1H); 3.21(s, 2H); 2.86(t, J=7.5 Hz, 4H); 2.13(s, 3H); 2.05(quint, J=7.5 Hz, 2H); 1.6(d, J=2 Hz, 3H) δ ppm NMR($^{13}$C, 90.5 MHz, CDCl$_3$): 168.3(s); 144.5(s); 142.2(s); 136.7(s); 131.1(d); 126.6(d); 124.7(d); 124.2(d); 121.5(s); 40.2(0; 32.8(t); 32.5(t); 25.5(t); 20.8(q); 13.6(q) δ ppm MS: 230(32), 188(53), 170(10), 160(10), 155(7), 145(11), 131(d); 77(6), 43(59)

EXAMPLE 15

Preparation of a perfuming composition

A base perfuming composition intended for a feminin type perfume was prepared by admixing the following ingredients:

| Ingredients | Parts by weight |
|---|---|
| Benzyl acetate | 15 |
| Geranyl acetate | 8 |
| Linalyl acetate | 35 |
| Styrallyl acetate | 4 |
| 10%* Cinnamic alcohol | 6 |
| 10%* Anisic aldehyde | 5 |
| Cyclosia ® Base[1] | 7 |
| 10%* Damascenone | 15 |
| 10% β-Dorinone ®[2] in ethyl citrate | 12 |
| Ethyl linalol | 20 |
| Eugenol | 25 |
| Exaltolide ®[3] | 17 |
| Galaxolide ®[4] 50 | 55 |
| Hedione ®[5] | 60 |
| Heliotropine | 44 |
| 10%* Hexylix ®[6] | 20 |
| 10% Indol in triethylamine | 32 |
| Iso E Super[7] | 100 |
| Levocitrol | 24 |
| Linalol | 20 |
| Phenethylol | 5 |
| 10%* Polysantol ®[8] | 60 |
| Polywood ®[9] Super | 15 |
| Benzyl salicylate | 110 |
| Pipol salicylate | 30 |
| 10%* Tagetes essential oil | 12 |
| α-Terpineol | 45 |
| 10%* Vanilline | 8 |
| α-Ionone | 14 |
| β-Ionone | 52 |
| Dianthine ®[10] SA | 5 |
| Total | 880 |

*in dipropyleneglycol (DIPG)
[1]hydroxycitronellal based mixture; origin: Firmenich SA, Geneva, Switzerland
[2]1-(2,2,6,6-trimethyl-1-cyclohexen-1-yl)-2-buten-1-one; origin: Firmenich SA, Geneva, Switzerland
[3]pentadecanolide; origin: Formenich SA, Geneva, Switzerland
[4]1,3,4,6,7,8-hexahydro-4,6,6,7,8,8-hexamethyl-cyclopenta-g-2-benzopyrane; origin: International Flavors & Fragrances Inc., USA
[5]methyl dihydrojasmonate; origin: Firmenich SA, Geneva, Switzerland
[6]allyl (cyclohexyloxy) acetate; origin: Charabot, France
[7]1-(octahydro-2,3,8,8-tetramethyl-2-naphthylenyl)-1-ethanone; origin: International Flavors &Fragrances Inc., USA
[8]3,3-dimethyl-5-(2,2,3-trimethyl-3-cyclopenten-1-yl)-4-penten-2-ol; origin: Firmenich SA, Geneva, Switzerland
[9]perhydro-5,5,8aα-trimethyl-2α-trans-naphtalenyl acetate; origin: Firmenich SA, Geneva, Switzerland
[10]origin: Formenich SA, Geneva, Switzerland To this base composition of the floral, green type, there were added, on the one hand 120 parts by weight of 3-(5-tert-butyl-2-methyl-1-phenyl)propanal according to the invention to prepare a novel composition A and, on the other hand, 120parts by weight of 3-(4-tert-butyl-1-phenyl)-2-methylpropanal, or LILIAL®, to prepare a composition B.

The two compositions were then evaluated on a blind test by a panel of 13 expert perfumers. According to the unanimous opinion of the latter, novel composition A was preferred for its much softer and natural floral note, relative to that of composition B. The perfumers also judged that the odor of composition A was more powerful and voluminous, its fragrance appearing as far more powdery, the jasmine and lily of the valley characters being distinctly exhalted.

When there were added to the base composition 120 parts by weight of 2-( 5-tert-butyl-2-methylbenzyl)propanal according to the invention, there was obtained a novel composition C, the odor of which was very similar to that of composition A, the floral note being nevertheless accompanied by a greener character.

EXAMPLE 16

Preparation of a perfuming composition

A base perfuming composition intended for a powder detergent was prepared by admixing the following ingredients:

| Ingredients | Parts by weight |
| --- | --- |
| Carbinol acetate | 15 |
| Linalyl acetate | 30 |
| (3 and 4)-(4-methyl-3-penten-1-yl)-3-cyclohexene-3-carbaldehyde | 20 |
| Amylcinnamic aldehyde | 125 |
| 50%* Undecylenic aldehyde | 15 |
| 50%* Methyl nonyl aldehyde | 15 |
| Citronellol | 15 |
| Dihydromyrcenol ®[1)] | 15 |
| 10%* Exaltolide ®[2)] | 30 |
| Beraniol brut | 30 |
| Heliotropine | 15 |
| Iralia ®[3)] | 90 |
| Linalol | 25 |
| Lorysia ®[4)] | 110 |
| Methyl methylanthranilate | 5 |
| Patchouli essential oil | 30 |
| Phenylhexanol | 25 |
| Polysantol ®[5)] | 20 |
| Polywood ®[6)] Super | 10 |
| Spiranol[7)] | 10 |
| Terpineol | 50 |
| Tonalid ®[8)] | 70 |
| Phenylacetaldehyde dimethylacetal | 10 |
| Vartofix couer[9)] | 40 |
| Dorinia SA[10)] | 20 |
| Galbex ®[11)] 183 | 10 |
| Total | 850 |

*in DIPG
[1)] 2,6-Dimethyl-7-octen-2-ol; origin: International Flavors & Fragrances Inc., USA
[2)] see example 3
[3)] methylionone (isomer mixture); origin: Firmenich SA, Geneva, Switzerland
[4)] 4-(1,1-dimethylethyl)-1-cyclohexyl acetate; origin: Firmenich SA, Geneva, Switzerland
[5)] see example 3
[6)] see example 3
[7)] 2,6,10,10-tetramethyl-1-oxaspiro[4.5]decan-6-ol; origin: Firmenich SA, Geneva, Switzerland
[8)] (5,6,7,8-tetrahydro-3,5,5,6,8,8-hexamethyl-2-naphthyl)-1-ethanone; origin: PFW, Holland
[9)] origin: Internaltion Flavors & Fragrances Inc., USA
[10)] origin: Firmenich SA, Geneva, Switzerland
[11)] origin: Firmenich SA, Geneva, Switzerland To this base composition of the floral type there were added 150 parts by weight of 5-tert-butyl-1-indancarbaldehyde to prepare a novel composition A and 150 parts by weight of 3-(4-tert-butyl-1-phenyl)-2-methylpropanal, or BOURGEONAL®, to prepare a composition B.

These two compositions were then used in identical concentrations to prepare two samples, respectively A and B, of a perfumed powder detergent. A panel of 7 perfumers, evaluating these two detergent samples on a blind test showed a clear preference for sample A, the odor of which was judged stronger and more elegant than that of sample B.

Two standard batches of textiles were then washed separately in two washing machines with the samples A and B and the odor of the textiles was evaluated on a blind test by a panel of six expert perfumers. The evaluation was carried out with the wet textiles, just out of the machine, as well as after 24 h of drying in air.

The perfumers unanimously preferred the odor of the textiles treated with sample A, both wet and after drying. The odor of this batch of textiles was judged distinctly superior, both in strength and quality, to that of the textiles washed with sample B.

The odor of the wet linen washed with sample A was judged much more floral than that of the textiles treated with sample B, whereas the dry textiles developed a much stronger odor, which odor also remained on the textiles for a far longer period of time than that of the textiles treated with sample B.

EXAMPLE 17

Stability test on smelling-strip

Stability tests on smelling strip were carried out by comparing the performance of certain compounds of the invention, i.e. 3-(5-tert-butyl- 2-methyl-1-phenyl)-1-propanal (smelling strip A), 3-(5-tert-butyl- 2-methylbenzyl)-1-propanal (smelling strip B), 5-tert-butyl- 2-indancarbaldehyde (smelling strip C) and 3-(3,3-dimethyl-5-indanyl)-1-propanal (smelling strip F), with that of their two known analogues, i.e. 3-(4-tert-butyl-1-phenyl)propanal or BOURGEONAL® (smelling strip D) and 3-(4-tert-butyl-1-phenyl)-2-methylpropanal or LILIAL® (smelling strip E).

Thus, a panel of 4 expert perfumers dipped the smelling strips into vials containing the above-mentioned compounds in a pure form, so as to obtain a soaked zone of about 1 cm in each case. These smelling strips were then evaluated on a blind test and their odors compared over time, this operation having been repeated every day, until the perfumers could no longer detect any odor from any of the smelling strips.

In their opinion, at the begining of the test, smelling strips A and B developed floral odors wherein the lily of the valley type connotation was distinctly dominant. In addition, smelling strip A developed a note which was reminiscent of the odor of thyme. As for smelling strip C, it developed a remarkably powerful floral note, with a greener character which was closer to the odor of BOURGEONAL®.

Smelling strip D had a far greener and aldehydic floral odor than that of smelling strips A and B, also more agressive, and smelling strip E had a floral odor of the same type as that of smelling strips A and B, but wherein the lily of the valley character was distinctly more marked.

Finally, smelling strip F developed a floral odor wherein the green connotation was very strong, such that it reminded one of the odor of freshly washed linen.

The evolution in time of the odor intensity of the six smelling strips, as judged by the perfumers on a value scale of 0 to 10, is indicated in the following table:

| Smelling strip | 3 days | 7 d | 9 d | 12 d | 15 d | 20 d |
| --- | --- | --- | --- | --- | --- | --- |
| A | 7 | 3 | — | — | — | — |
| B | 6 | — | — | — | — | — |
| C | 5 | 5 | 5 | 4 | 4 | 3 |
| D | 8 | 4 | — | 1 | — | — |
| E | — | — | — | — | — | — |
| F | 7 | — | 6 | 4 | 4 | 3 |

Thus, it was observed that smelling strips A and B, which at the begining developed odors close to that of smelling strip E, and at least as strong, kept this odor for about 5 days, whereas the odor of smelling strip E decreased strongly in the first 24 h and could no longer be detected at the end of 3 days. On the other hand, smelling strip D kept a strong odor at the end of 3 days, which however abated rapidly within the following week, whereas smelling strip C, whose odor intensity was at the begining inferior to that of smelling strip D, but similar, kept henceforth a practically stable intensity and still developed a perfectly perceptible fragrance 20 days after having been dipped in 5-tert-butyl-2-indancarbaldehyde according to the invention. Furthermore, according to the perfumers, the quality of the odor of smelling strip C had suffered no deterioration whatsoever at the end of this period.

Similar behaviour was observed with smelling strip F which conserved its odor for more than a month, thus revealing the remarkable tenacity of the 3-(3,3-dimethyl-5-indanyl)-1-propanal according to the invention.

EXAMPLE 18

Test of stability against oxidation by gas phase chromatography (GC)

The qualitative evolution described in the preceding example for 3-(5-tert-butyl-2-methyl-1-phenyl)-1-propanal and its prior art analogues, on the basis of the perfumers' odor evaluation, was entirely confirmed, in a quantitative manner, by means of gas phase chromatography (GC) measurements. The following method was applied.

Onto standard smelling strips (7×147 mm) there was deposited a drop of respectively 3-(5-tert-butyl-2-methyl-1-phenyl)-1-propanal (smelling strip A), 3-(4-tert-butyl-1-phenyl)propanal or BOURGEONAL® (smelling strip B) and of 3-(4-tert-butyl-1-phenyl)-2-methylpropanal or LILIAL® (smelling strip C).

The thus soaked zone of the smelling strips (~20 mm) was cut and immersed for 1 h in $CH_2Cl_2$ (1 ml) contained in closed test tubes, with occasional stirring.

Before injecting the solutions in a GC apparatus, bis-(trimethylsilyl)-acetamide (Aldrich, 4 drops, ~30 mg) was added to each of the three solutions, to form the trimethylsilylic ester of the acid into which the aldehyde extracted from each of the smelling strips had been converted by air oxidation. It had in fact been observed that the GC signal of said esters was distinctly less broad than that of the corresponding acids, thus allowing a far more precise integration.

The three solutions were then injected into a GC apparatus ($SiO_2$, 10 m column) at regular time intervals, adapted to the oxidation speed observed for each of the three above-mentioned aldehydes. The signals corresponding to the aldehyde and the trimethylsilyl ester (the latter being proportional to the amount of formed acid) were integrated and the results obtained represented on the graph of FIG. 1.

On this graph, the percentage of aldehyde and corresponding acid are represented as a function of time. The curves represented translate the average values obtained in two distinct experiments, carried out with each of the compounds whose structures are represented.

It is clearly apparent from FIG. 1 that the compound according to the invention, i.e. 3-(5-tert-butyl-2-methyl-1-phenyl)-1-propanal, is far more stable against air oxidation than its known isomer 3-(4-tert-butyl-1-phenyl)-2-methylpropanal or LILIAL®, which, at the end of about 4 days, has been converted to the extent of 80% into the corresponding acid, which is practically odorless.

When comparing the compound of the invention with its known lower homologue, i.e. the 3-(4-tert-butyl-1-phenyl)propanal or BOURGEONAL® (origin: Naarden Int., Holland), again it can be clearly seen that the latter, although far more stable than LILIAL®, has been converted up to 70% into the corresponding acid at the end of about 20 days, whereas the aldehyde according to the present invention is still ~60% stable.

Figure 2:
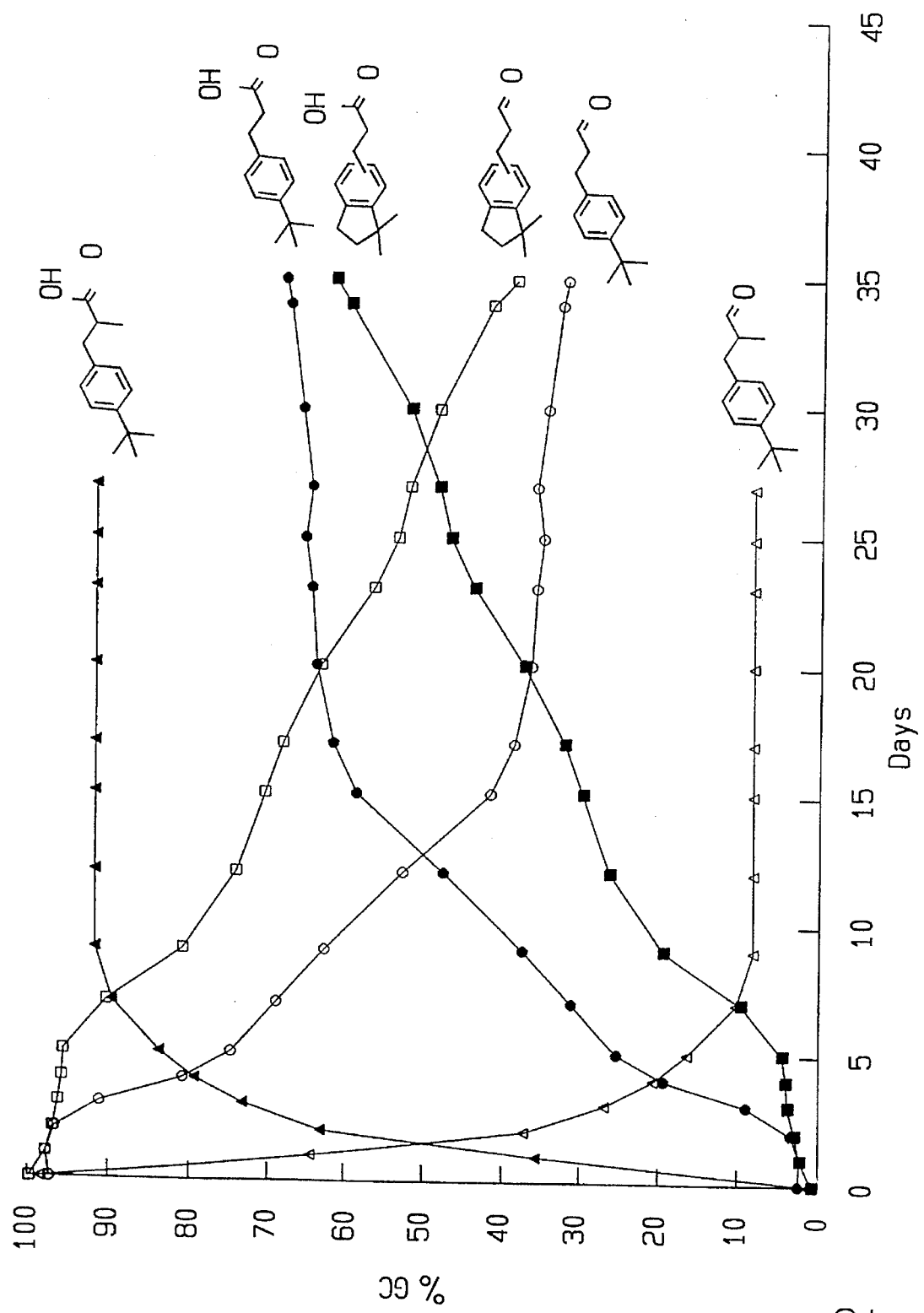

Analogous tests were carried out with another compound of the invention, i.e. 3-(3,3-dimethyl-5-indanyl)-1-propanal, and the results, represented in FIG. 2, also show that this compound is more stable against oxidation than the two known compounds cited above.

It should be noted that these results cannot be imputed to differences in volatility and/or polarity of the compounds of the invention relative to their known analogues LILIAL® and BOURGEONAL®. We have in fact measured the retention times of these two compounds in two types of (GC) columns (100°14 20°, 10°/min), and the results presented hereinafter show that there are no significant differences in these values.

| Retention time GC [min] | LILIAL ® | BOURG-EONAL ® | 3-(5-tert-butyl-2-methyl-1-phenyl) propanol | 3-(3,3-dimethyl-5-indanyl) propanol (2 isomers) |
|---|---|---|---|---|
| Silica column (10 m) | 4.01 | 4.10 | 4.34 | 5.03; 5.17 |
| Carbowax column (10 m) | 5.62 | 5.69 | 6.78 | 6.46; 6.80 |

EXAMPLE 19

Perfuming composition for a powder detergent

A base perfuming composition intended for a powder detergent was prepared by admixture of the following ingredients:

| Ingredients | Parts by weight |
|---|---|
| Benzyl acetate | 200 |
| Linalyl acetate | 70 |
| Verdyl acetate | 160 |
| Anisic aldehyde | 60 |
| 10%* Decanal | 10 |
| Hexylcinnamic aldehyde | 300 |
| 10%& Methylnonyl aldehyde | 10 |
| Methyl anthranilate | 25 |
| Astronone[1] | 150 |
| Coranol[2) 3)] | 50 |
| Allyl cyclohexylpropanoate | 10 |
| 10%* Ethylvanilline | 70 |
| Hedione ®[3) 4)] | 100 |
| Heliotropine | 25 |
| Galaxolide 50[5) 6)] | 380 |
| Iralia ® Total[3) 7)] | 600 |
| Iso E Super[5) 8)] | 250 |
| Koavone[5) 9)] | 70 |
| Methylnaphthylketone | 10 |
| p-tert-Butylcyclohexanone acetate | 250 |
| Phenylhexanol | 30 |
| Verdyl propanoate | 100 |
| Amyl salicylate | 60 |
| Galbex ® 183[3)] | 10 |
| Total | 2000 |

*in DIPG
[1)]ethylene undecane dicarboxylic
[2)]4-cyclohexyl-2-methyl-2-butanol
[3)]origin: Firmenich SA, Geneva, Switzerland
[4)]methyl 3-oxo-2-pentyl-cyclopentylacetate
[5)]origin: International Flavors & Fragrances Inc., USA
[6)]1,3,4,6,7,8-hexahydro-4,6,6,7,8,8-hexamethyl-cyclopenta-g-2-benzopyrane
[7)]iso-methylene-ionone
[8)]7-acetyl-1,2,3,4,5,6,7,8-octahydro-1,1,6,7-tetramethyl-naphthalene
[9)]acetyl-diisoamylene When there are added to 30 parts by weight of the composition thus obtained 3 parts by weight of 3-(3,3-dimethyl-5-indanyl)-1-propanal, there is obtained a novel composition having a distinctly enhanced green note. In addition, the composition acquires a marked fresh character. Such an olfactive note was as well developed in a powder detergent, as in the wet linen washed with the detergent perfumed by means of said novel composition.

Once dried, the linen (after 24 h) had a typical aldehydic, green fresh odor, which instantly aroused in the user a pleasant sensation of very clean linen. Upon adding to the base composition the same proportion of 5-tert-butyl-2-indancarbaldehyde an olfactive effect similar to that described above was obtained, albeit slightly less powerful, whereas the addition of the same amount of 6-tert-butyl-1-indanacetaldehyde imparted to the composition a more pronounced odor of the green-leafy type, wherein the aldehydic-lily of the valley character was not as perceptible as in the case of the addition of the two compounds above-cited.

EXAMPLE 20

Perfuming base

A base composition of the floral, woody type, intended for a soap, was prepared by admixing the following ingredients:

| Ingredients | Parts by weight |
| --- | --- |
| Benzyl acetate | 250 |
| Citronellyl acetate | 150 |
| Phenylethyl acetate | 120 |
| Styrallyl acetate | 100 |
| Anisic aldehyde | 100 |
| 50%* Undecylenic aldehyde | 120 |
| Hexylcinnamic aldehyde | 200 |
| 4-(4-hydroxy-1-phenyl)-2-butanone | 5 |
| Citronellol | 150 |
| Dihydromyrcenol[1) 5)] | 200 |
| 10%* Ethylvanilline | 30 |
| Eugenol | 60 |
| Lilial ®[2)] | 120 |
| Hedione ®[3) 4)] | 100 |
| 10%* Methyl-p-cresol | 40 |
| Vertofix coeur[5)] | 430 |
| Iralia ® Total[3) 6)] | 130 |
| γ-Undecalactone | 5 |
| Phenethylol | 300 |
| Phenylhexyl phenylacetate | 20 |
| p-tert-Butylcyclohexanone acetate | 750 |
| Polysantol ®[1) 3)] | 20 |
| Verdyl propanoate | 250 |
| Hexyl salicylate | 400 |
| Tonalid ®[1)] | 100 |
| Violet essential oil | 20 |
| Ylang synth. | 50 |
| Total | 4220 |

*in DIPG
[1)] see example 16
[2)] origin: Givaudan-Roure, Vernier, Switzerland
[3)] origin: Firmenich SA, Geneva, Switzerland
[4)] methyl 3-oxo-2-pentyl-cyclopentylacetate
[5)] origin: International Flavors & Fragrances Inc., USA
[6)] iso-methyl-ionone The addition, to this base composition, of 80 parts by weight of 6-tert-butyl-1-indanacetaldehyde imparted thereto an aldehydic-green note that recalled the olfactive effect that one can achieve with BOURGEONAL®, whereas adding the same amount of 5-tert-butyl-2-indancarbaldehyde or of 3-( 3,3-dimethyl-5-indanyl)-1-propanal produced a clearly distinct floral-lily of the valley effect, all the more powerful in the latter case. This latter compound also imparted to the base composition, in a more marked manner, a pleasant fresh, clean linen character.

What we claim is:

1. A compound of formula

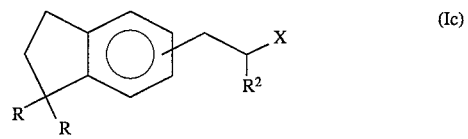

wherein X represents a —CHO group or a group of formula —CH (OR')$_2$ in which R', taken separately, each represent a C$_1$ to C$_4$ linear or branched alkyl radical, or taken together represent a C$_2$ to C$_4$ alkylene radical, R$^2$ represents a hydrogen atom or a methyl radical, and R represents a hydrogen atom or a methyl radical, the groups R being identical or different.

2. The compound of claim 1, selected from the group consisting of:

h. 3-(3,3-diméthyl-5-indanyl)propanal;

i. 3-(1,1-diméthyl-5-indanyl)propanal;

j. 3-(5-indanyl)propanal; and k. 3-(4-indanyl)propanal.

3. A method to confer, improve, enhance or modify the odor properties of a perfuming composition or a perfumed article, which method comprises adding to said composition or article a fragrance effective amount of a compound according to claim 1.

4. A perfuming composition or a perfumed article which contains as an active perfuming ingredient a compound according to claim 1.

5. A perfumed article according to claim 4, in the form of a perfume, a cologne, a soap, a bath or shower gel, a shampoo or other hair-care product, a cosmetic preparation, a body deodorant or an air-freshener, a detergent or a fabric softener, or a household product.

6. A method to confer, improve, enhance or modify the odor properties of a perfuming composition or a perfumed article, which method comprises adding to said composition or article a fragrance effective amount of a compound according to claim 2.

7. A perfuming composition or perfumed article which contains as an active perfuming ingredient a compound according to claim 2.

* * * * *